US006316250B1

(12) United States Patent
Hjelle et al.

(10) Patent No.: US 6,316,250 B1
(45) Date of Patent: Nov. 13, 2001

(54) MOLECULAR CLONES PRODUCING RECOMBINANT DNA ANTIGENS OF THE HANTAVIRUS-ASSOCIATED RESPIRATORY DISTRESS (HARDS)

(75) Inventors: Brian Hjelle; Steve Jenison, both of Albuquerque, NM (US)

(73) Assignee: The University of New Mexico, Albuquerque, NM (US)

( * ) Notice: Subject to any disclaimer, the term of this patent is extended or adjusted under 35 U.S.C. 154(b) by 0 days.

(21) Appl. No.: 09/106,075

(22) Filed: Jun. 29, 1998

Related U.S. Application Data

(60) Division of application No. 08/210,762, filed on Mar. 22, 1994, now Pat. No. 5,837,441, and a continuation-in-part of application No. 08/141,035, filed on Oct. 26, 1993, now abandoned, which is a continuation-in-part of application No. 08/120,096, filed on Sep. 13, 1993, now abandoned, and a continuation-in-part of application No. 08/111,519, filed on Aug. 25, 1993, now abandoned.

(51) Int. Cl.$^7$ .................................................. C12N 15/40
(52) U.S. Cl. .................. 435/320.1; 435/69.3; 536/23.72
(58) Field of Search ........................ 536/23.72; 435/69.3, 435/320.1; 935/73, 69, 70

(56) References Cited

U.S. PATENT DOCUMENTS 5,298,423 * 3/1994 Dalrymple ......................... 435/320.1
5,945,277 * 8/1999 Nichol et al. ............................ 435/5

OTHER PUBLICATIONS

Alter, 1991, Descartes before the Horse: I Clone, Therefore I Am: The Hepatits C Virus in Current Perspective, Annals of Internal Medicine 115:644–649.

Balnaves et al., 1991, Direct PCR from CVS and blood lysates for detection of cystic fibrosis and Duchenne muscular dystrophy deletions, Nucleic Acids Research 19:1155.

Choo, et al., 1989, Isolation of a cDNA Clone Derived from a Blood–Borne Non–A, Non–B Viral Hepatitis Genome, Science 244:359–362.

Henikoff, 1984, Unidirectional digestion with exonuclease III creates targeted breakpoints for DNA sequencing, Gene 28:351–359.

Holton et al., 1991, A simple and efficient method for direct cloning of PCR products using ddT–tailed vectors, Nucleic Acids Research 19:1156.

Koerner, et al., 1991, High–Expression Vectors with Multiple Cloning Sites for Construction of trpE Fusion Genes pATH Vectors, Methods in Enzymology 194:477–490.

Marchuk, et al., 1991, Construction of T–vectors, a rapid and general system for direct cloning of unmodified PCR Products, Nucleic Acids Research 19:1154.

Sarkar, et al., 1990, Shedding light on PCR Contamination, Nature 343:27.

* cited by examiner

*Primary Examiner*—Donna C. Wortman
(74) *Attorney, Agent, or Firm*—Morgan, Lewis & Bockius, L.L.P.

(57) ABSTRACT

The invention provides HARDS virus rDNA for expression in molecular clones. The expressed products are useful in immunodiagnostics, prophylactics, and therapeutics for the HARDS virus and related hantaviruses. Of particular interest are a type-specific epitope of the HARDS virus G1 protein, and dominant epitopes of the HARDS virus N protein cross-reactive with antibodies to the HARDS virus and the related hantavirus PHV, both expressed by cDNA clones according to the invention.

13 Claims, 24 Drawing Sheets

S SEGMENT CLONE

CODING SEQUENCE: N PROTEIN

1 — 143 — 1272 — 1697

H — REGION CLONED — X pCR II PLASMID VECTOR

FIG. 1

M SEGMENT CLONES

CODING SEQUENCE:

G1 GLYCOPROTEIN → | G2 GLYCOPROTEIN → CDC SEQ.

1317 — "3H226 M 2038" — 3355

1 — "3H226 G1 1275" — 1407 × 1535 — "3H226 M 1225" — 2760 — 3398 — 3707

132 — 3004 — MHAR G2 392

H — REGION CLONED — X pCR II PLASMID VECTOR

FIG. 2

RECOMBINANT ANTIGENS: CONTEMPLATED USES

| G1 | G2 | HARDS |
| M SEGMENT |

1. DESIGN PRIMERS BASED ON RELATED VIRUSES
2. PCR

PCR PRODUCT

CLONE

USE AS Ag IN DIAGNOSTIC TEST

EXPRESS PROTEIN IN
E. coli,
BACULOVIRUS
OR VACCINIA VIRUS

USE AS Ag IN IMMUNIZATIONS AND FOR VACCINES

```
NMHV                                                                    1
PHILL     QQQTSQRATTSAGMSQLRETQEEITRHEQQLVIARQKLKEAERTVEVDPDDVNKSTLQS
          *  *  ::  *    ************:*:*******:****  *** ****  ****
PUUMALA            MSDLTDIQEEITRHEQQLVVARQKLKDAERAVEVYPDDVIKNTLQA
                   1         10        20        30        40
CONSENS            MS+L  +   QEEITRHEQQLV!ARQKLK+AER VEV PDDV KSTLQ S

NMHV                                                          1
                                                              STLQS
                                                              *****
PHILL                                                         STLQS
                                                              *****
PUUMALA
                                                  50        60
CONSENS

NMHV      RRAAVSALETKLGELKRELADLIAAQKLASKPVDPTGIEPDDHLKEKSSLRYGNVLDVNS
          ** *******:** *********  *****:** ************:*******:****
PHILL     RRSAVSTLEDKLAEFKRQLADVISRQKMDEKPVDPTGIELDDHLKERSSLQYGNVLDVNS
          *  *** ****** **:***:*  *: *** ************ ********:******
PUUMALA   RQQTVSALEDKLADYKRRMADAVSRKKMDTKPTDPTGIEPDDHLKERSSLRYGNVLDVNA
          10        20        30        40        50        60
CONSENS   RR AVSALEDKLA+%K

FIG. 5B

```
               70        80        90        100       110       120
NMHV     IDLEEPSGQTADWKSIGLYILSFALPIILKALYMLSTRGRQTIKENKGTRIRFKDDSSYE
         ** **********  ** **  ********** *********:*****************
PHILL    IDIEEPSGQTADWLKIGSYIIEFALPIILKALHMLSTRGRQTVKENKGTRIRFKDDSSYE
         *************  ** *:* *  ******* *********************** *:*
PUUMALA  IDIEEPSGQTADWYTIGVYVIGFTIPIILKALYMLSTRGRQTVKENKGTRIRFKDDTSFE
          110       120       130       140       150       160
CONSENS  IDIEEPSGQTADW  IG Y!I FALPIILKALYMLSTRGRQT!KENKGTRIRFKDDSS%E
                130       140       150       160       170       180

130       140       150       160       170       180
NMHV     EVNGIRKPRHLYVSMPTAQSTMKADEITPGRFRTIACGLFPAQVKARNIISPVMGVIGFS
         :***** * ***************:* ******** *******: **************
PHILL    DVNGIRRPKHLYVSMPTAQSTMKAEELTPGRFRTIVCGLFPAQIMARNIISPVMGVIGFA
         *:**************************************  **  *** *********
PUUMALA  DINGIRRPKHLYVSMPTAQSTMKAEELTPGRFRTIVCGLFPTQIQVRNIMSPVMGVIGFS
          170       180       190       200       210       220
CONSENS  +!NGIRRPKHLYVSMPTAQSTMKA+ELTPGRFRTIVCGLFPAQ! ARNIISPVMGVIGFS
                190       200       210       220       230       240
```

FIG. 5C

```
                190       200       210       220       230       240
NMHV     FFVKDWMERIDDFLAARCPFLPEQKDPRDAA.....LATNRAYFITRQLQVDESKVSDIE
         *****  ::   ****   ::       *        *      8**    **    ::
PHILL    FFVKDWADKVKAFLDQKCPFLKAEPRPGQPAGEAEFLSSIRAYLMNRQAVLDETHLPDID
         *****  ::   ****   ::  :                *         ***    ***
                230       240       250       260       270       280
PUUMALA  FFVKDWPEKIREFMEKECPFIKPEVKPGTPAQEVEFLKRNRVYEMTRQDVLDKNHVADID
CONSENS  FFVKDW  +K!  +F$+    CPF LK +    PG+PA  E  EFL  NRAYFMTRQ  VLDE   HV   DI+
                250       260       270       280       290       300

250       260       270       280       290       300
NMHV     DLIADARAESATIEADIATPHSVWVFACAPDRCPPTALYVAGMPELGAFFAILQDMRNTI
         *:   *          *  ** *   *  ************** ************
PHILL    ALVELAASGDPTLPDSLENPHAAWVFACAPDRCPPTCIYIAGMAELGAFFAILQDMRNTI
         *:::  ******   **  ** *   *  ************* *************
                290       300       310       320       330       340
PUUMALA  KLIDYAASGDPTSPDDIKSPNAPWVFACAPDRSPPTCIYVAGMAELGAFFSILQDMRNTI
CONSENS  L!+  AASGDPT PDDI  PHA WVFACAPDRCPPTCIY!AGMAELGAFFAILQDMRNTI
                310       320       330       340       350       360
```

FIG. 5D

```
                 310       320       330       340       350   356
NMHV       MASKSVGTSEEKLKKKSAFYQSYLRRTQSMGIQLDQKIIILYMSHWGREAVNHFHL
           **** *** ************************* ** :**  ** * ******
PHILL      MASKTVGTAEEKLKKKSAFYQSYLRRTQSMGIQLDQRIILMYMIEWGNEVVNHFHLGDDM
           ************* ** *********************:** *** * *:********
PUUMALA    MASKTVGTAEEKLKRKSSFYQSYLRRTQSMGIQLDQRIILLYMLEWGKEMVDHFHLGDDM
            350       360       370       380       390      400
CONSENS    MASKTVGTAEEKLKKKSAFYQSYLRRTQSMGIQLDQRIILSYM EWG E V+HFHLGDDM
                  370       380       390       400       410       420

NMHV

PHILL      DPELRQLAQALIDQKVKEISNQEPLKIOOPACIASTFIAYISSCLLOFIITIIIQVIVML
           ***** *** *****************                 *
PUUMALA    DPELRGLAQSLIDQKVKEISNQEPLKIO................L
            410       420       430                 435
CONSENS    DPELR LAQ LIDQKVKEISNQEPLKIO                L
                  430       440       450       460       470       480
```

FIG. 5E

```
NMHV
PHILL      ISLTNSQLNIALNQHLGTQLMEQYCKTELSLQFISVFIISKATTYLNTLIYMHVAYIQVY
PUUMALA
CONSENS              490       500       510       520       530       540

NMHV
PHILL      IYYLNSVFSQLLFKEYTT
PUUMALA
CONSENS    550       558
```

FIG. 6A

```
              1         10        20        30        40        50        60
HARDS         GLGQGYVTGSVETTPILLTQVADLKIESSCNFDLHVPATTQKYNQVDWTKKSSTTESTN
              ***   ** *  *  * ::  *      ******   *   *      *  *   *
PHILL         GLGQGLVIGTVDLNPVPVESVSTLKLESSCNFDVHTSSATQQAVTKWTWEKKADTAETAK
              ***   ** *  *  * ::  *  *   ******     *   *  ****** *   *
PUUMALA       RLGQGLVVGSVELPSLPIQQVETLKLESSCNFDLHTSTAGQQSFTKWTWEIKGDLAENTQ
              ***   **      *      *  *   ******         *  ****
              1         10        20        30        40        50        60
CONSENS       GLGQGLV!GSV+L P!P!+QV TLKLESSCNFDLHTS ATQQ  °%TKWTWEKK DTAE T+
              1         10        20        30        40        50

70        80        90        100       110       120
HARDS         AGATTFEAKTKEINLKGTCNIPPTTFEAAYKSRKTVICYDLACNQTHCLPTVHLIAPVQT
              * **::  *  *  ***** * *     *   ***  *****  ** ******   *  
PHILL         AASTTFQSKSTELNLRGLCVIPTLVLETANKLRKTVTCYDLSCNQTACIPTVYLIAPIHT
              * **::  *  *  ***** * *     *   **** ******  ** ****** * *
PUUMALA       ASSTSFQTKSSEVNLRGLCLIPTLVVETAARMRKTIACYDLSCNQTVCQPTVYLMGPIQT
              70        80        90        100       110       120
CONSENS       A STTF+ KS E!NLRGLC IPTLV ETA K$RKT! CYDLSCNQT C PTVYLIAP!QT
              70        80        90        100       110       120
```

FIG. 6B

```
                        130            140            150            160            170
HARDS      CMSVRXYI.GLLSSRIQVIYEKTYCVTGQLIEGLCFIPTHTIALTQPGHTYDXMTLPVTC
              *    *  ****** ******  ** * ***** *    **   * ****
PHILL      CVTTKSCLLGLGTQRIQVTYEKTYCVSGQLVEGTCFNPIHTMALSQPSHTYDIVTIPVRC
           *:************ ***** ************* ****** *********:*:**** *
PUUMALA    CITTKSCLLSLGDQRIQVNYEKTYCVSGQLVEGICFNPIHTMALSQPSHTYDIMTMMVRC
           * ********* ** ******* ************:************:**:**** *
CONSENS    C!TTKSCLLGLG QRIQV YEKTYCVSGQL!EG  CFNPIHTMALSQPSHTYDIMT$PVRC
                        130            140            150            160            170

190            200            210            220            230
HARDS      FLVAKKL..GTQLKLAVELEKLITGVSCTENSFQGYYICFIGKHSEPLFVPTMEDYRSAE
             *  :   **   * *** ** *  *:****** ******  **** *****::*: *
PHILL      FFIAKK.TNDDTLKIEKQFETILEKSGCTAANIKGYYVCFLGATSEPIFVPTMDDFRASQ
           * :  ** *   *    *:*  * ::*  *  :**** **  *** *****  *:*
PUUMALA    FLVIKKVTSGDSMKIEKNFETLVQKNGCTANNFQGYYICLIGSSSEPLYVPALDDYRSAE
           *:  ** *   :: *** ***::** *****  ***** *:   *** **  * **:*
CONSENS    FL!AKK T  GD  $KIEK+FETL!+K  GCTANNFQGYY!CFIG   SEPL&°VPT$+D°°RSA+
                 190            200            210            220            230
```

FIG. 6C

```
            240       250       260       270       280       290
HARDS       LFTRMVLNPRGEDHDPDQNGQGLMRIAGPVTAKVPSTETTETMQGIAFAGAPMYSSFSTL
                *   * *****         ****    * ****  :* **:** * *:* * * *
PHILL       ILSDMAISPHGEDHDSALSSVSTFRIAGKLSGKAPSTESSDTVQGVAFSGHPLYTSLSVL
            :** **  *******     **  *****  **************:**** *****  **
PUUMALA     VLSRMAFAPHGEDHDIEKNAVSAMRIAGKVTGKAPSTESSDTVQGIAFSGSPLYTSTGVL
                   250       260       270       280       290       300
CONSENS     !LSRMA  PHGEDHD + N VS MRIAGKVTGKAPSTESS+TVQG!AFSG P$YTS SVL
                   250       260       270       280       290       300

300       310       320       330       340       350
HARDS       VRKADPEYVFSPGIIAESNHSVCDKKTVPLTWTGFLAVSGEIEKITGCTVFCTLAGPGAS
              * ** *: ***** * ** ****** ******:*   * *** * **:*********
PHILL       ASKEDPVYIWSPGIIPERNHTVCDKKTLPLTWTGYLPLPGGIEKTTQCTIFCTLAGPGAD
             **:****** **** * ** :*:**********:  *** ********:**********
PUUMALA     TSKDDPVYIWAPGIIMEGNHSICEKKTLPLTWTGFISLPGEIEKTTQCTVFCTLAGPGAD
                   310       320       330       340       350       360
CONSENS      SK+DPVY!WSPGII E NHS!C+KKTLPLTWTG%L LPGEIEKTTQCT!FCTLAGPGAD
                   310       320       330       340       350       360
```

FIG. 6D

```
             360         370         380         390         400       407
HARDS        CEAYSETGIFNISSPTCLVNKVQKFRGSEQRINFMCQRVDQDVVVYCNGQ
             ****.:*****************:*  **  * ******:******
PHILL        CEAYSDTGIFNISSPTCLINRVQRFRGAEQQIKFVCQRVDLDIVVYCNGM
             *****.************************.:*************
PUUMALA      CEAYSETGIFNISSPTCLINRVQRFRGSEQQIKFVCQRVDMDITVYCNGM
                         370         380         390         400       410
CONSENS      CEAYS+TGIFNISSPTCL!NRVQRFRGSEQQIKFVCQRVD$D!VVYCNGM
                         370         380         390         400       410
```

FIG. 7

```
AGCACATTAC AGAGCAGACG GGCAGCTGTG TCTGCATTGG AGACCAAACT CGGAGAACTC
ACAGGGATTG AACCTGATGA CCATTTAAAG GAAAAATCAT CACTGAGATA TGGAAATGTC
CTTGATGTAA ATTCCATTGA CCTAGAAGAA CCAAGTGGGC AAACAGCTGA TTGGAAATCC
ATCGGACTCT ACATTCTAAG TTTTGCATTA CCGATTATCC TTAAAGCCTT GTACATGTTA
TCTACTAGAG GCCGTCAAAC AATCAAAGAA AACAAGGGAA CAAGAATTCG ATTTAAGGAT
GATTCATCTT ATGAAGAAGT CAATGGAATA CGTAAACCAA GACATCTATA TGTTTCTATG
CCAACTGCTC AGTCTACAAT GAAAGCAGAT GAGATTACTC CTGGGAGGTT CCGTACAATT
GCTTGTGGGT TATTCCCGGC CCAAGTCAAA GCAAGGAATA TTATCAGTCC TGTTATGGGT
GTGATTGGCT TTAGTTTCTT TGTGAAAGAT TGGATGGAAA GAATTGATGA CTTTCTGGCT
GCACGTTGTC CATTCTACC CGAACAGAAA GACCCTAGGG ATGCTGCATT GGCAACTAAC
AGAGCCTATT TTATAACACG TCAATTACAG GTTGATGAGT CAAAGGTTAG TGATATTGAG
GATCTAATTG CTGATGCAAG GGCTGAGTCT GCCACTATAT CGCCACTCCT
CATTCAGTTT GGGTCTTCGC ATGTGCTCCA GATCGTTGTC CACCTACAGC ATTATATGTG
GCCGGGATGC CGGAGTTGGG TGCATTTTTT GCTATTCTTC AGGATATGAG GAACACCATA
ATGGCATCAA AATCTGTGGG GACATCTGAA GAGAAATTGA AGAAAAATC AGCATTCTAC
CAGTCATACT TGAGACGTAC TCAGTCAATG GGGATTCAAC TGGACCAGAA GATAATCATC
TTATACATGA GCCATTGGGG AAGAGAGGCC GTCAATCACT TCCATCTT
```

FIG. 9

```
GGTTTAGCTC AGGGTTACGT GACAGGTTCA GTGGAAACTA CACCTATTCT CTTAACGCAG
GTAGCTGATC TTAAGATTGA GAGTTCTTGT AATTTCGATC TGCATGTCCC GGCTACTACT
ACCCAAAAAT ACAATCAGGT TGACTGGACC AAAAAAAGTT CAACTACAGA AAGCACAAAT
GCAGGTGCAA CTACATTTGA GGCTAAAACA AAAGAGATAA ATTTAAAAGG CACATGTAAT
ATTCTTCCAA CTACATTTGA AGCTGCATAT AAATCAAGGA AGACAGTAAT TTGTTATGAT
TTAGCCTGTA ATCAAACACA TTGTCTTCCT ACAGTCCATT TGATTGCTCC TGTTCAAACG
TGCATGTCTG TGCGGAGCTG TATGATAGGT TTGCTGTCAA ACAGGATTCA AGTCATATAT
GAGAAGACAT ACTGTGTTAC AGGTCAATTA ATAGAGGGGC TATGTTTCAT CCCAACACAT
ACAATTGCAC TCACACAACC TGGTCATACC TATGATACTA TGACATTGCC AGTGACTTGT
TTTTAGTAG CTAAAAAGTT GGGAACACAA CTTAAGCTGG CTGTTGAGTT AGAGAAACTG
ATTACTGGTG TGAGTTGCAC AGAAAACAGC TTTCAAGGTT ACTACATCTG CTTTATCGGA
AAACATTCAG AGCCCTTATT TGTGCCAACA ATGGAAGATT ATAGGTCAGC TGAGTTATTT
ACCCGTATGG TTTTAAATCC GAGAGGTGAA GATCATGACC CTGATCAAAA TGGACAAGGC
TTAATGAGAA TAGCCGGACC TGTTACAGCT AAGGTGCCAT CTACAGAAAC TGGACAAGGC
ATGCAAGGAA TTGCATTTGC TGGGGCACCG ATGTATAGCT CTTTCTCAAC TCTCGTGAGG
AAGGCTGATC CTGAGTATGT CCTTCTCCCCA GTGTATAATTG CAGAATCAAA TCATAGTGTC
TGTGATAAGA AAACAGTACC CCTTACATGG ACAGGGTTTT TGGCAGTTTC TGGAGAGATA
GAGAAAATAA CAGGCTGTAC AGTCTTCTGT ACATTGGCAG GACCTGGTGC TAGTTGTGAA
GCATACTCAG AAACAGGAAT CTTTAATATA AACTTCATGT GCCAAAGAGT GAATAAAGTT
CAAAAATTCA GAGGCTCAGA ACAGAGAATC AACTTCATGT GCCAAAGAGT TGATCAAGAT
GTTGTAGTCT ATTGTAATGG GCAA*
```

FIG. 10

```
ATGAGCACCC TCAAAGAAGT GCAAGACAAC ATTACTCTCC ACGAACAACA ACTTGTGACT
GCCAGGCAGA AGCTCAAAGA TGCAGAAAGA GCGGTGGAAT TGGACCCCGA TGATGTTAAC
AAAAGCACAT TACAGAGCAG ACGGGCAGCT GTGTCTGCAT TGGAGACCAA ACTCGGAGAA
CTCAAGCGGG AACTGGCTGA TCTTATTGCA GCTCAGAAAT TGGCTTCAAA ACCTGTTGAT
CCAACAGGGA TTGAACCTGA TGACCATTTA AAGGAAAAAT CATCACTGAG ATATGGAAAT
GTCCTTGATG TAAATTCCAT TGACCTCGAG GAACCAAGTG GGCAAACAGC TGATTGGAAA
TCCATCGGAC TCTACATTCT AAGTTTTGCA TTACCGATTA TCCTTAAAGC CTTGTACATG
TTATCTACTA GAGGCCGTCA AACAATCAAA GAAAACAAGG GAACAAGAAT TCGATTTAAG
GATGATTCAT CTTATGAAGA AGTCAATGGA ATACGTAAAC CAAGACATCT ATATGTTTCT
ATGCCAACTG CTCAGTCTAC AATGAAAGCA GATGAGATTA CTCCTGGGAG GTTCCGTACA
ATTGCTGTGT GGTTATTCCC GGCCCAAGTC ATATTATCAG AAAGCAAGGA TCCTGTTATG
GGTGTGATTG GCTTTAGTTT CTTTGTGAAA AAAGAATTGA GATTGGATGG TGACTTTCTG
GCTGCACGTT GTCCATTTCT ACCCGAACAG GATTGGATGG AAAGAATTGA ATTGGCAACT
AACAGAGCCT ATTTTATAAC ACGTCAATTA AAAGACCCTA CAGGTTGATG TAGTGATATT
GAGGATCTAA TTGCTGATGC AAGGGCTGAG CAGGTTGATG AGTCAAAGGT TATCGCCACT
CCTCATTCAG TTTGGTCTTT CGCATGTGCT TCTGCCACTA TATTCGCAGA GTCCGCCACT
GTGGCCGGGA TGCCGAGTT GGGTGCATTT CCAGATCGTT GTCCACCTAC AGCATTATAT
ATAATGGCAT CAAAATCTGT GGGACATCT TTTGCTATTC TTCAGGATAT GAGGAACACC
TACCAGTCAT ACTTGAGACG TACTCAGTCA GAAGAGAAAT TGAAGAAAAA ATCAGCATTC
ATCTTATACA TGAGCCATTG GGGAAGAGAG GCCGTGAATC ACTTCCATCT T
```

FIG. 11A

```
ATGAGCACCC TCAAAGAAGT GCAAGACAAC ATTACTCTCC ACGAACAACA ACTTGTGACT
GCCAGGCAGA AGCTCAAAGA TGCAGAAAGA GCGGTGGAAT TGGACCCCGA TGATGTTAAC
AAAAGCACAT TACAGAGCAG ACGGGCAGCT GTGTCTGCAT TGGAGACCAA ACTCGGAGAA
CTCAAGCGGG AACTGGCTGA TCTTATTGCA GCTCAGAAAT TGGCTTCAAA ACCTGTTGAT
CCAACAGGGA TTGAACCTGA TGACCATTTA AAGGAAAAAT CATCACTGAG ATATGGAAAT
GTCCTTGATG TAAATTCCAT TGACCTCGAG
```

FIG. 11B

```
                v              v              v              v              v
MSTLKEVQDNITLHEQQLVTARQKLKDAERAVELDPDDVNKSTLQSRRAAVSALETKLGELKREL
       v              v              v              v
ADLIAAQKLASKPVDPTGIEPDDHLKEKSSLRYGNVLVVNSIDL
```

FIG. 12A
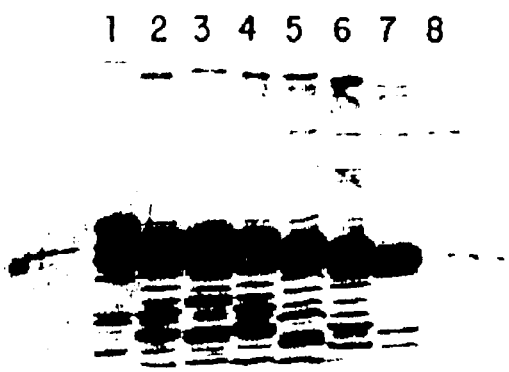
FIG. 12B
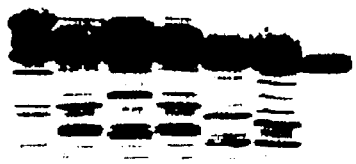
FIG. 12C

FIG. 13A

TAGTAGTAGACTCCGCAAGAAGAAGCAAACACTGAATAAAGGAGATACAGAATGGTAGGGTGGGTTTGCA 70

TCTTCCTGTGTCCTTACTACTGCAACTGCGGGCTAACACGGAATCTTTATGAGTTGAAGATAGAATG 140

TCCACACATACTGTAGGTTTAGGTCAGGGTTACGTGACAGGTTCAGTGAAACTACACCTATTCTTAACG 210

CAGGTAGCTGATCTTAAGATTGAGAGTTCTTGTAATTCGATCTGCATGTCCCGGCTACTACTACCCAAA 280

AATACAATCAGGTTGACTGGACCAAAAAAGTTCAACTACAGAAAGCACAAATGCAGGTGCAACTACATT 350

TGAGGCTAAACAAAAGAGATAAATTTAAAGGCACATGTAATATTCCTCCAACTACATTTGAAGCTGCA 420

TATAAATCAAGGAAGACAGTAATTTGTTATGATTAGCCCTGTAATCAAACACATTGTCTTCCTACAGTCC 490

ATTTGATTGCTCCTGTTCAAACGTCCATGTCTGTGCCGAGCTGTATGATAGGTTTGCTGTCAAGCAGGAT 560

FIG. 13B

```
TCAAGTCATATATGAGAAGACATACTGTGTTACAGGTCAATTAATAGAGGGGCTATGTTTCATCCCAACA    630
CATACAATTGCACTCACACAACCTGTCATACCTATGATACTATGACATTGCCAGTGACTTGTTTTTAG     700
TAGCTAAAAAGTTGGGAACACAACTTAAGCTGGCTGTTGAGTTAGAGAAACTGATTACTGGTGTGAGTTG   770
CACAGAAAACAGCTTTCAAGGTTACTACATCTGCTTTATCGGAAAACATTCAGAGCCCTTATTGTGCCA    840
ACAATGGAAGATTATAGGTCAGCTGAGTTATTTACCCGTATGGTTTAAATCCGAGAGGTGAAGATCATG    910
ACCCCTGATCAAAATGGACAAGGCTTAATGAGAATAGCCGGACCTGTTACAGCTAAGGTGCCATCTACAGA  980
AACAACGAAACAATGCAAGGAATTGCATTGCTGGGGCACCGATGTATAGCTCTTTCTCAACTCTCGTG    1050
AGGAAGGCTGATCCTGAGTATGTCTTCTCCCCAGTATAAATTGCAGAATCAAATCATAGTGTCTGTGATA  1120
```

FIG. 13C

```
AGAAAACAGTACCCCTTACATGGACAGGGTTTTTGGCAGTTTCTGGAGAGATAGAGAAAATAACAGGCTG    1190

TACAGTCTTCTGTACATTGGCAGGACCTGGTGCTAGTTGTGAAGCATACTCAGAAACACAGAATCTTTAAT    1260

ATAAGCTCTCCTACTTGTTTGGTGAATAAAGTTCAAAAAATTCAGAGGCTCAGAACAGAGAATCAACTTCA    1330

TGTGCCAAAGAGTTGATCAAGATGTTGTAGTCTATTGTAATGGGCAAAAGAAAGTCATTCTTACCAAAAC    1400

TCTGGTCATAGGCCCAATGTATTTATACATTCACTAGTTTATTCTCACTAATCCTAGGAGTTGCCCATTCT   1470

CTTGCCGTAGAGCTAGTGTTCCAGGTCTTCATGGCTGGGCTACAACAGCATTACTGATTACTTTTGCT      1540

TTGGCTGGCTCCTTATACCGACAGTCACCTTAATTATACTAAAGATCCTGAGGTTGCTCACTTCTCATG    1610

CTCACATTATTCTACAGAATCAAAATTCAAAGTTATCTTAGAAAGAGTTAAGTTGAATACCAAAAAACA    1680
```

FIG. 13D

```
ATGGGCTCTATGGTGTGTGATATTTGCCACCATGAATGCCAAAGAGAACTTGAAACACATAAGA   1750
AAAGCTGTCCAGAAGGTCAATGCCCGTATTGTATGACAATAACTGAATCCACTGAGATGGCTCTTCAAGC   1820
CCATTTTGCAATCTGTAAGTTAACAAACAGGTTTCAGGAAAACTTAAAAAATCATTAAAACGCCCAGAA   1890
GTACGGAAAGGTTGTTACAGGACACTGGGAGTTTTTAGATACAAGAGCAGATGTTATGTTGGTTTAGTAT   1960
GGGGAATTCTTTTAACAACTGAACTGATCATATGGGCCAGCCAGTGCAGAAACCCCCTTAATGGAGTCTGG   2030
TTGGTCTGACACAGCGCATGGTGTGGGCATAATTCCTATGAAGACAGATTTGGAGCTTGACTTTGCATCG   2100
GCCTCATCATCTTCTTACAGTTATAGGCGAAAGCTTATAAACCTGCTAATCAAGAAGAAACACTCCCTT   2170
TTCATTTCCAGTTAGACAAACAAGTAGTGCATGCAGAGATCCAGAACCTAGGACATTGGATGATGGTAC   2240
```

FIG. 13E

```
ATTCAACATAAAAACTGCTTTCACTGTTATGGGAGTGTAAAAATATGCCTATCCTTGGCAAACAGCC      2310
AAGTGCTTCTTTGAAAAGGATTATCAGTATGAAACAAGTGGGGCTGTAATCCACCAGACTGTCCAGGGG    2380
TAGGTACAGGTTGTACAGCTTGTGGGGTGTATCTCGATAAGTCCCGTTCGGTTGGGAAAGCATACAAGAT   2450
AGTATCACTCAAATACACACGGAAGGTGTATTCAATTAAGGAACAGAAAAACTTGTAAACATATAGAT     2520
GTAAATGATTGCTTGGTTACCCCTTCTCGTCAAAGTTGTATGATCGGTACTATATCAAAGCTCCAACCAG  2590
GTGATACTTTGTTGTTCTTAGGCCCTTAGAGCAGGTGGGATTATCCTTAAGCAATGTGTACAACATC     2660
ATGTGTGTTTGGAGACCCCGGTGATATTATGTCAACGACAAGTGGGATGAGGTGCCCAGAACATACTGGA  2730
TCTTTTTAGAAAGATATGTGGGTTTGCTACAACATTGAGTATCAAGGCAACACAGTGTCTGGGT        2800
```

FIG. 13F

```
TCAAACGCATGATGGCAACTCGAGATTCTTCCAATCATTCAATGTGACAGAACCACATATCACTAGCAA    2870
CCGACTTGAGTGCATTGATCCAGATAGCAGTATCAAAGATCATATTAATATGTTTAAATCGGATGTT    2940
TCCTTTCAGGATCTAAGTGATAACCCATGCAAGGTTGATCTGCATATACAATCAATTGATGGGCCTGGG    3010
GTTCAGGGGTAGGTTTTACGTTGGTATGCACTGTGGGGCTTACAGAGTGTGCAAATTTATAACTTCAAT    3080
TAAAGCATGTGATTCTGCCATGTGTTATGGAGCCACAGTGACAAATCTGCTTAGAGGGTCAAACACAGTT    3150
AGAGTTGTGGTAAAGTGGGCATTCTGGATCTTTGTTTAAATGCTGCAATGATACTGACTGTACCGAAG    3220
AAGGTTTAGCAGCATCCACCACATTTAGATAGGGTTACAGTGTCACAATCAAATAGATTCTGATAAAGT    3290
TTATGATGAGCTTGCACCGCCCTGTACAATCAAGTGTTGTTTAAAAAATCTGGGAATGG    3351
```

MOLECULAR CLONES PRODUCING RECOMBINANT DNA ANTIGENS OF THE HANTAVIRUS-ASSOCIATED RESPIRATORY DISTRESS (HARDS)

This application is a divisional of Ser. No. 08/210,762, filed Mar. 22, 1994, issued Nov. 12, 1998, U.S. Pat. No. 5,837,441, and a continuation-in-part of Ser. No. 08/120,096, filed Sep. 13, 1993, abandoned, and a continuation-in-part of Ser. No. 08/111,519, filed Aug. 25, 1993, abandoned, and a continuation-in-part of Ser. No. 08/141,035, filed Oct. 26, 1993, abandoned.

The research leading to these inventions was supported by the United States Government, and the Government has certain rights in this Patent.

BACKGROUND OF INVENTION

1. Field of Art

The invention relates to the HARDS virus, the etiologic agent of Hantavirus-Associated Respiratory Distress Syndrome.

An epidemic of unexplained adult respiratory distress syndrome, affecting primarily residents of the Four Corners region formed by the borders of New Mexico, Arizona, Utah, and Colorado, was recognized in May, 1993. The disease is characterized by a prodromal illness of fever, myalgias, and, in some cases, conjunctivitis, lasting 1–5 days, followed by a severe and acute illness characterized by pulmonary edema and shock. According to the federal Centers for Disease Control and Prevention (CDC), through Jul. 27, 1993, death from suffocation and/or shock had occurred in 14 (78%) of the 18 patients diagnosed with the illness since the epidemic was recognized. The syndrome was eventually determined to be caused by a viral infection of a newly-identified hantavirus virus subsequently named the HARDS virus (also referred to as Sin Nombre Virus and Four Corner Virus, or FCV). According to the CDC, the predominant vector for this virus is the deer mouse Peromyscus maniculatus, which ranges throughout the southwest U.S. with the potential for spreading HARDS infection within this area.

The infection involves two clinical stages. In the first stage, or prodrome, nonspecific abnormalities such as fever, muscle aches, and cough occur, making the distinction between HARDS virus infection and influenza, "Strep throat", and other upper respiratory infections difficult. The prodromal infection lasts only briefly, and is followed in 1–5 days by the second stage of HARDS virus infection, characterized by severe pulmonary disease and shock that often proves fatal. By the time pulmonary edema appears, it is often possible to distinguish HARDS infection from infection caused by other microbes, but many authorities consider that stage to be too late for HARDS virus to be effectively treated by antivirals having potential anti-HARDS activity.

Accordingly, the need for a rapid diagnostic test for the presence of the HARDS virus is particularly acute. In addition to assisting clinicians in determining which patients are infected with HARDS virus and in need of hospitalization and treatment, a specific test for HARDS virus would guide public health officials in their efforts to monitor the extent and spread of the disease. A specific test for HARDS vipus would also be helpful for rodent surveillance, studies of the prevalence and transmission of HARDS virus infection, and many other research activities. Such a test would make possible the determination of the range of HARDS virus in rodent populations, thus documenting precisely which human populations are at risk for HARDS infection.

2. Discussion of Related Art

1. Viral Characterization

By early June, it was recognized that the victims of the new syndrome were developing, during their illness, IgM antibodies that reacted with one or both of two members of the Hantavirus genus of Bunyaviruses. Those viruses are known as Puumala virus, a vole virus that causes the human disease nephropathia epidemica (Europe), and Seoul virus, a virus of Norwegian rats first identified in Korea. Scientists at the federal Centers for Disease Control and Prevention (CDC), in Atlanta, Ga., were able to obtain molecular clones and limited sequence information from the new virus. The sequence information supported the notion that the new virus is a hantavirus; and suggested that its closest relatives among the hantaviruses might be Puumala virus, and another rodent virus known as Prospect Hill virus (PHV).

2. Diagnosis of HARDS Virus Infection

The standard method for diagnosis of acute infections caused by other hantaviruses is the detection, via enzyme-linked immunosorbent assay (EIA), of IgM antibodies to the suspected virus. To do this, it is necessary to have the suspected virus growing in tissue culture; such infected cell cultures are the source of viral antigens to which the patient's serum Igm will react. Thus, for example, serum from a patient with suspected infection by Hantaan virus (which occurs in Korea and China) is incubated with lysate of Hantaan virus-infected cells, and the immune complexes are detected by another antibody.

Despite many attempts to grow the HARDS virus in culture by CDC and others, suitable cultures for the production of viral antigens for the assay of immunoreactive serum antibodies have not been achieved, and thus far, infection by HARDS virus has been diagnosed by one of the following routes:

(a) The development, in infected patients, of antibodies to HARDS virus that can be shown to "cross-react" weakly with antigens derived from Puumala virus or Seoul virus. This method is useful for epidemiologic surveillance, but has proved to be insufficiently sensitive to allow diagnosis of HARDS infection before the patient becomes either critically ill and near death, or has recovered from infection. Infection by HARDS virus appears to result in a somewhat less brisk antibody response than that seen in association with infection by other hantaviruses.

(b) Polymerase chain reaction (PCR). CDC scientists developed a PCR method for diagnosing HARDS infection in June, 1993. A small portion of the G2 gene of the viral M segment is copied into DNA using the enzyme reverse transcriptase, and amplified into large amounts of DNA. The amplified DNA (185 bp) is detected on an agarose gel. Application of this technique to patients presenting to the UNM Hospital in Albuquerque, N.Mex. have shown that the HARDS virus can be detected in the peripheral blood cells of ~90% of infected patients, with no known false-positive tests thus far. The method is somewhat slow (36 hours between receipt of blood and detection of the virus) and appears to be subject to false-negative tests, probably attributable to a sufficient difference in viruses between affected patients to prevent the annealing of PCR primers.

An additional concern in use of PCR is false-positive tests. This problem arises when tiny amounts of amplified viral DNA, present in the laboratory on surfaces, centrifuges, gel apparatuses, etc., finds its way into test tubes used in the preparation of a PCR reaction. The contaminating DNA makes an excellent template for the next PCR reaction, making false-positive tests in uninfected patients a significant risk. The risk can be reduced substantially by strict and rigorous physical separation of facilities used for "pre-PCR" activities (for example, areas where RNA is prepared from the blood of patients to be tested for HARDS virus), and "post-PCR" activities, where amplified viral DNA is studied and analyzed. However, such separation may not be sufficient. In many cases, it is helpful to irradiate PCR cocktails—prior to amplification—with ultraviolet light to destroy contaminating template DNAs, before the bona fide target (patient RNA) is added. However, UV irradiation is much more effective in situations where the contaminating DNA is expected to be at least 300 bases long; for this reason, any contamination by the 185 base-pair product produced by the CDC protocol is unlikely to be "sterilized" sufficiently by UV irradiation. This requirement for larger PCR target is shared by many of the most successful schemes for PCR decontamination (*Nature* 343:27, 1990).

The expense, slow turnaround time, and labor-intensiveness of PCR (as presently configured) makes it a suboptimal solution for rapid diagnosis of hantavirus infection. Nevertheless, PCR may be the best solution available before a definitive serologic (antibody or antigen) test becomes available.

(c) Immunohistochemistry. It is possible to detect HARDS virus antigens in tissue samples of infected patients by exposing the tissues (lungs or kidneys) to a specific monoclonal antibody, originally raised against Puumala virus. This method has been used by CDC in patient tissues obtained at autopsy, but has not been shown to be an effective means of diagnosis in fresh blood samples from living patients.

It is accordingly desirable to provide a rapid method for detecting RNA from the HARDS virus or antibodies to the HARDS virus, especially for clinical serological tests. A reliable source of plentiful amounts of highly antigenic viral antigens suitable for immunoassay applications is particularly desirable.

BRIEF DESCRIPTION OF THE DRAWING

FIG. 1 illustrates the 1129 nt clone obtained from the S segment of the HARDS virus from patient 3H226. PHV S segment coordinates of the clone are 141–1272. H, Hind III site; X, Xba I site;

FIG. 2 illustrates M segment clones obtained from the HARDS virus. Four clones containing a total of 3264 nt in four overlapping pieces of viral sequence were obtained. The location of the 241 nt of sequence provided by the CDC is also shown;

FIG. 3 illustrates uses of the recombinant DNA (rDNA) of the invention;

FIG. 5 shows an alignment of the protein encoded by the HARDS virus clone p3H226 S 1129 CR-7 ("NMHV") (SEQ ID NO:18) with those of its closest known hantavirus relatives, Prospect Hill Virus ("PHILL"; GenBank X55128) (SEQ ID NO:86) and Puumala virus strain P360 ("PUUMALA"; GenBank X61035) (SEQ ID NO:87). Regions of identity are indicated with asterisks. Note that many regions of great similarity are present, for example, the highly homologous domain between NMHV coordinates 37 and 193. These regions are the most likely locus for epitopes that are broadly cross-reactive; other regions, such as those between amino acids 194 and 264, are more diverged and will prove to subtend type-specific epitopes within N;

FIG. 6 shows an alignment of the protein (partial sequence) encoded by the HARDS virus clone p3H226 G1 1275 CR-1 ("HARDS") (SEQ ID NO:88) with those of its closest known hantavirus relatives, Prospect Hill Virus ("PHILL", GenBank X55129) (SEQ ID NO:89) and Puumala virus strain P360 ("PUUMALA", L08755) (SEQ ID NO:90). In this domain of G1, no broadly-reactive epitopes have been encountered; instead at least one potent epitope that appears to be specific to HARDS infection has been found. Note several regions of significant divergence between HARDS virus and its relatives, such as coordinates 36 through 93;

FIG. 7 shows the complete nucleotide sequence of the p3H226 S 1129 CR-7 clone subtended by primers used in its amplification (SEQ ID NO:18).

FIG. 9 shows the complete nucleotide sequence of the FCV-specific portion (lacking primer sequences used in amplification) of p3H226 G1 1275 CR-1. Sequence of the DNA encoding the dominant epitope (the amino acid sequence SCNFDLHVPATTTQKYNQVDWTKKSS (SEQ ID NO: 12)) (SEQ ID NO:10) is bolded;

FIG. 10 shows the complete nucleotide sequence of the FCV DNA insert of p3H226 S 1229 pATH-7, which was constructed by ligation of FCV sequences amplified from p3H226 S 419 CR-1 and p3H226 S 1129 CR-7 (SEQ ID NO:20). The artificially-modified sequence that specifies an Xho I site (but does not modify the protein encoded by the N gene) is bolded;

FIG. 11 shows a nucleotide sequence of the clone p3H226 S 317 (SEQ ID NO:21) (A) corresponding to amino acids 1–100 (SEQ ID NO:22) (B) of the dominant N protein epitope;

FIG. 12 shows a Western immunoblot showing reactivity of a carboxy-to-amino terminal nested deletion series derived from p3H226 S 317 pATH-1 with two HARDS patient sera (panels A and B) or a control serum (panel C). Expressed proteins include that from p3H226 S 317 pATH-1 itself (lane 1), as well as a series of 6 proteins of decreasing size that continued to react with the HARDS patient serum antibodies (lanes 2–8). The carboxy-terminus of the dominant epitope of FCV N protein is encoded by the DNA sequence that is present in clone 7 but lacking in clone 8; and FIG. 13 illustrates a sequencing of the majority of the FCV (3H226) M segment (SEQ ID NO:23).

SUMMARY OF THE INVENTION

Figure 4:
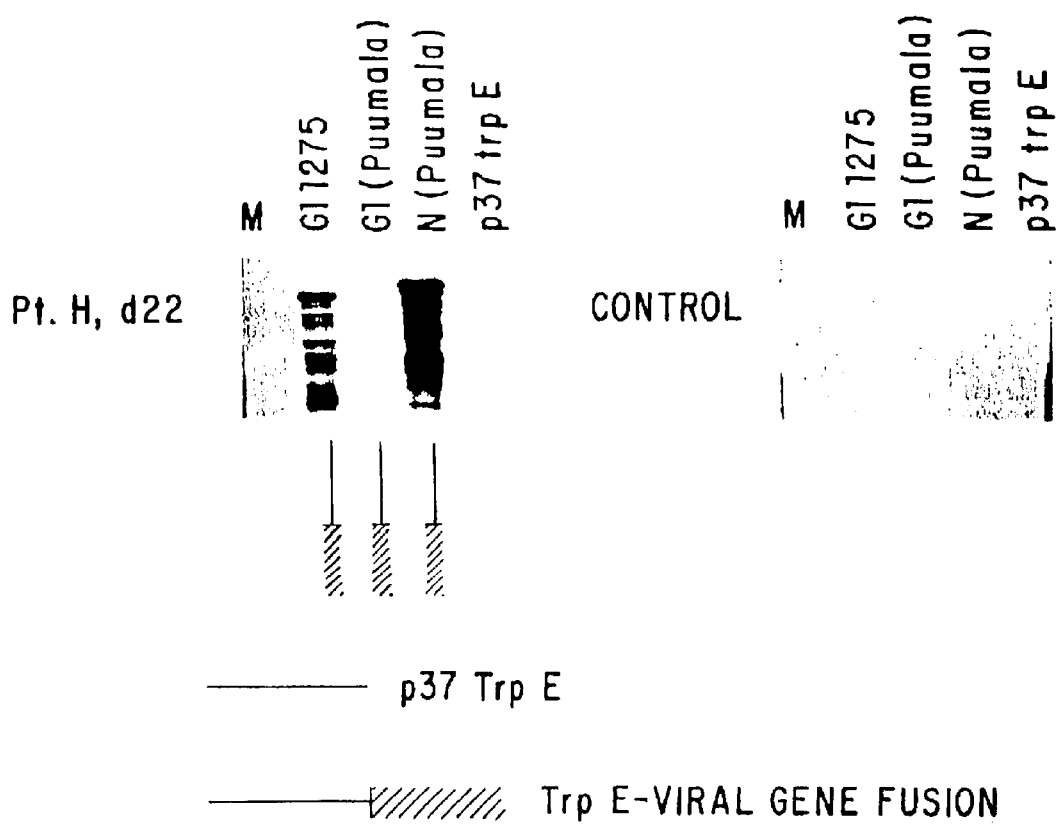
FIG. 4 is serum from patient H (who had recently recovered from a clinically typical case of HARDS) was used to probe a western blot membrane containing a lysate of insoluble protein fraction derived from *E. coli* cultures induced to express trp E protein molecules to which the following viral proteins have been appended as fusion moieties: (a) that protein encoded by the 1275 nt of HARDS virus G1 gene in the clone p3H226 G1 1275 CR-1; (b) the entire G1 gene of Puumala virus strain P360; (c) the entire N protein of Puumala virus strain P360; and (d) the protein p37$^{trp\ E}$ with no fused viral domain. M=molecular weight markers, which bands do not reproduce in this illustration. The blot was probed successively with patient serum, alkaline phosphatase-conjugated goat anti-human IgG, then a color reagent to detect alkaline phosphatase. Patient H's serum reacted briskly to HARDS G1 protein but not at all to the G1 protein of the related Puumala virus. Patient H serum also reacted strongly to Puumala virus N protein. Uninfected human control serum recognized no protein, and neither serum recognized Trp E protein by itself.

The invention provides molecularly cloned viral DNA inserts encoding for one or more highly antigenic protein domains of the HARDS virus. The expression of these inserts in suitable expression vectors permits the production of large amounts of viral proteins or oligopeptides from the N, G1, and G2 capsid antigens of the HARDS virus, and identification and isolation of immunodominant and type-specific viral epitopes. The proteins/oligopeptides of the invention may also be synthesized by conventional methods.

The resulting antigens are especially useful in immunoassays for the presence of HARDS antibodies (for example, in patient blood samples), and for the production of antibodies to the HARDS virus in immunosystems for the diagnosis, treatment and prophylaxis of HARDS virus infection.

DETAILED DESCRIPTION OF THE INVENTION

Of the 3 segments of the hantavirus genome, the M segment (encoding the envelope glycoproteins G1 and G2) and S segment (encoding the nucleocapsid protein, N), appear to encode all or nearly all of the important antigens of the hantavirus capsid. In the present effort, the great majority of the coding sequence of the M and S segments of the HARDS virus (FIGS. 1 and 2) was molecularly cloned, using as template viral RNAs of patients infected with HARDS.

Clones were obtained as follows. By scanning the nucleotide sequences of the complementary DNAs of the M and S segments of Puumala and PHV (publicly available, published information available through the GenBank sequence database, at the NCBI [National Center for Biotechnology Information], a service of the National Library of Medicine [National Institutes of Health], Rockville, Md.), numerous short regions of ~20 nt of sequence conserved between the two viruses were identified. On the theory that any new hantavirus of this serotype might also have retained these conserved sequences, DNA oligonucleotides that corresponded to these sequences or their complements were prepared. Various combinations of such oligonucleotides were used as primers in reverse transcription/polymerase chain reactions (see Examples); the HARDS virus template was provided by lung RNAs from patients 3H226 and MHAR who had died with typical clinical features and pathologic findings of HARDS virus infection (New Mexico Office of the Medical Investigator). Primers were designed to produce a PCR product that would easily clone into bacterial expression vectors, i.e., plasmids-designed to allow the ready production of the protein encoded by the foreign DNA insert.

Polymerase chain reactions of the type employed herein to amplify selected DNA oligonucleotide sequences (or their complements) are well-known in the art, and any suitable method may be employed. Alternatively, unamplified sequences may be used, as well as any other method which provides or selected DNA sequence for reaction against a HARDS viral RNA template to provide the insert of the invention.

Primer pairs for use in the PCR/reverse transcription systems are selected for good amplification of the DNA regions of interest, and for the production of easily cloned PCR products. Various methods of cloning PCR products are known in the art, and any suitable method may be used. A particularly useful method known as "TA cloning" (for the introduction of a single T:A base pair between a vector restriction site and a PCR product) is described in *Nucl. Acids Res.* 19: 1154, 1156 (1991); other useful PCR cloning methods are also described and referenced therein. TA cloning can be done "from scratch", or commercially available cloning systems, such as the TA Cloning Kit available from Invitrogen, may be employed.

As known in the art, the PCR products are cloned into expression vectors to direct the production of large amounts of antigenic viral protein. various expression vectors may be employed, including bacterial expression vectors (plasmids) and vectors for eukaryotic cells, such as baculovirus and expression vectors for yeast and mammalian cells, which tend to improve duplication of post-translational modifications such as glycosylation of the native viral proteins. The invention is not broadly dependent upon the methods employed to produce the molecular clones of the invention, nor upon the expression vectors or host cells employed, and those recited are exemplary. Protein expression can be optimized by trial and error application of a variety of promoters and host cell strains until high-level expression of the protein encoded by the hantavirus inserts is obtained. Exemplary promoters include the trp E promoter in conjunction with a pATH series of vectors to produce high-expression vectors with multiple cloning sites for construction of trp E fusion proteins (*Methods Enzymol.* 194: 477–90, 1991); or DHFR (Qiagen, Inc., Chatsworth, Calif.); mal E (New England Biolabs Inc., Beverly, Mass.); or bacteriophage T7 (Dr. W. Studler, Cold Spring Harbor Laboratory, Cold Spring Harbor, N.Y.).

After subcloning the cloned PCR product (PCR product ligated to expression vector) into the corresponding host cell, the cells are screened in conventional manner to select clones directing high expression of protein of high antigenicity and specificity, or other characteristics relevant to the intended application. Screening for immunocharacteristics is readily done in conventional manner by assaying the recombinant antigen against HARDS virus antibodies in immunoassay procedures such as enzyme-linked immunoassays, radioimmunoassays or immunoblot (see, e.g., *Science* 244: 359–362, 1989 and *Ann. Int. Med.* 115: 644–649, 1991).

In one embodiment of the invention, after trying multiple primer pairs, ten primer pairs were identified that successfully amplified (and allowed the cloning of) the five large regions that were judged to encode one or more dominant epitopes (highly antigenic protein domains) of the HARDS virus. These regions include a portion of the S segment (FIG. 1) that encodes nearly all of the nucleocapsid protein "N" (the cDNA/mRNA coordinates 141 through 1272 of PHV; the precise coordinates of the HARDS virus itself are not yet known but probably will be similar to those of PHV); and M segment domains (FIG. 2) bounded by coordinates 132 through 1407 of PHV (clone "3H226 G1 1275"); 1535 through 2760 of PHV ("3H226 M 1225"); 1317 through 3355 ("3H226 M 2038") and 3004 through 3396 of PHV ("MHAR G2 392"). The 241 nt of HARDS virus sequence lying between coordinates 2762 and 3003 (FIG. 2) was provided to the inventor by the CDC.

All of the five regions ("inserts") described above were cloned into the cloning vector pCRII (Invitrogen Corp.) by TA cloning. All inserts were subcloned into bacterial expression vectors pATH10, pATH21, pATH23 and/or pQE60, for the purpose of "expressing" (making in large quantities) the proteins encoded by the DNA inserts.

The Examples provide details of the methods employed.

Utility of the Invention

The products of the invention, including HARDS viral rDNA per se, the DNA inserts (HARDS viral cDNA ligated to an expression vector, including viral cDNA PCR products), and host cells containing the DNA inserts, are broadly useful in the production of antigenic proteins or oligopeptides for diagnostic, prophylactic, and therapeutic applications, particularly immunoassays for, and protective vaccines against, the HARDS virus. Antigenic epitopes according to the invention include both type-specific epitopes highly specific to the HARDS virus, and dominant epitopes strongly reactive with the HARDS virus and other hantavirus such as the Prospect Hill virus. The N protein antigens, in combination with G1 protein antigens, should prove to be particularly useful in detecting and characterizing infections with divergent strains of HARDS virus, particularly for antigenic variations within G1-enclosed type-specific antigen occurring between different virus strains.

Antibody/Antigen Affinity Pairs

The large amounts of homologous viral protein available from the molecular clones of the invention, selected for desired properties, lends the invention to clinical immunoassays and immunotherapies employing either the rDNA antigens or antibodies (both monoclonal and polyclonal) raised against the antigens by known techniques. Immunoassays employing tracer-labelled antibody or antigen such as EIA, ELISA, RIA, RIBA, immunofluorescent assays, and western blot assays are exemplary, as are affinity purifications, standard agglutination and immuno-precipitation assays.

Serologic assays employing DNA antigen for detecting the presence of antibodies to the HARDS virus in blood samples of mammals, either clinically or for assessing the spread of disease in vectors are of particular interest. A detailed description of one such serological assay is set forth in Example III. Also of particular interest is the use of DNA antigen for amplification of a specific signal in such a EIA system. Antibodies complementary to rDNA antigen of the invention are sources of passive immunization to the HARDS virus; such prophylactic interventions after viral exposure have previously been employed in connection with exposure to rabies and hepatitis B virus.

Antibodies to rDNA antigen are readily prepared by textbook procedures such as those described in Methods in Immunology, Garvey et al, eds; W. A. Benjamin, Inc., Reading, Mass. 19777, incorporated herein by reference.

Utility of the HARDS virus rDNA described herein in immunoassays is of great importance owing to the present unavailability of native BARDS virus antigens derived from cultured cells. However, even if such tissue cultures are developed, the rDNA antigens of the present invention will often prove superior to native antigens, as the recombinant antigens can be designed for particular tasks such as discrimination between closely related viruses, with reliable and reproducible results.

Use in Development of Vaccines

Molecular clones encoding a majority of the antigenic domains of the HARDS virus are important vaccine reagents. For example, the HARDS antigen(s) can be expressed in cultured cells under the control of a vaccinia or other heterologous virus' replication machinery, and used to prepare live or killed-virus vaccinia antigens in accordance with known principles. Further, HARDS virus DNA can be used as a substrate for "naked DNA vaccines", e.g., immunization by injection of purified HARDS virus DNA intramuscularly into humans or animals. Additionally, purified HARDS virus proteins, expressed in baculovirus, yeast, or $E.$ $coli$, can be used to immunize humans or animals. As known in the art, immunogenicity of the antigens may be boosted, if necessary, by coupling to haptens. The vaccines of the invention may comprise type-specific epitopes, or combinations of type-specific and cross-reactive epitopes.

EXAMPLES

Section I

I. Experimental Methods

A. Design of PCR Primers

The following regions were identified as candidates for primer synthesis by alignment between the Prospect Hill Virus M segment ("PHV"; GenBank accession X55129) and the M segment of Puumala strain K27 ("PUUM"; GenBank accession M14627) as regions with a high degree of nucleotide sequence homology:

|  | Name or Coordinate | Sequence (5' to 3') | | | | | | | | |
|---|---|---|---|---|---|---|---|---|---|---|
| PHV | 1 | TAG | TAG | TAG | ACT | CCG | CAA | GAA | GA | (SEQ. ID NO:24) |
| PUUM | 1 | TAG | TAG | TAG | ACT | CCG | CAA | GAA | GA | (SEQ. ID NO:25) |
| Primer | "HanM1+" | TAG | TAG | TAG | ACT | CCG | CAA | GGA | GA | (SEQ. ID NO:26) |
| PHV | 132 | AGA | TTG | AAT | GTC | CTC | ATA | CTG | TA | (SEQ. ID NO:27) |
| PUUM | 132 | AAA | TGG | AAT | GTC | CAC | ATA | CTA | TT | (SEQ. ID NO:28) |
| Primer[a] | "HanMG1NT" | A CCA | TGG | AAT | GTC | CTC | ATA | CTG | TA | (SEQ. ID NO:29) |
| PHV | 1363 | TGT | GTA | CTG | TAA | TGG | CAT | GAA | GAA | (SEQ. ID NO:30) |
| PUUM | 1367 | TGT | TTA | CTG | TAA | TGG | GAT | GAA | GAA | (SEQ. ID NO:31) |
| Primer[b] | "HanM1363+" | TGT | (GT)TA | CTG | TAA | TGG | (CG)AT | GAA | GAA | (SEQ. ID NO: 32) |
| PHV | 1382 | AAG | AAG | GTA | ATT | CTT | ACT | AAA | ACC CT | (SEQ. ID NO: 33) |
| PUUM | 1385 | AAG | AAA | GTC | ATT | CTC | ACC | AAG | ACC CT | (SEQ. ID NO: 34) |
| Primer[b,c] | "HanM1406-" | AAG | AA(GA) | GT(AC) | ATT | CTT | ACT | AAA | ACC CT | (SEQ. ID NO: 35) |

-continued

| Name or Coordinate | Sequence (5' to 3') | |
|---|---|---|
| PHV | 1535 | ACA TTC TGT TTT GGC TGG (SEQ. ID NO:36) |
| PUUM | 1538 | ACA TTC TGT TTT GGC TGG (SEQ. ID NO:37) |
| Primer | "G1P53N0I" | ACA TTC TGT TTT GGC TGG (SEQ. ID NO:38) |
| PHV | 1693 | ATG GTC TGT GAG GTT TGT CAG (SEQ. ID NO:39) |
| PUUM | 1696 | ATG GTT TGT GAA GTG TGT CAG (SEQ. ID NO:40) |
| Primer[b,c] | "HanM1716-" | ATG GT(CT) TGT GA(GA) GTT TGT CAG (SEQ. ID NO:41) |
| PHV | 2738 | TTT AGA AAG AAA TGT GCA TTT GC (SEQ. ID NO:42) |
| PUUM | 2741 | TTT AGA AAG AAA TGT GCA TTT GC (SEQ. ID NO:43) |
| Primer[c] | "HanM2739-" | TTT AGA AAG AAA TGT GCA TTT GC (SEQ. ID NO:44) |
| PHV | 3004 | TGG TGC ATG GGG CTC AGG (SEQ. ID NO:45) |
| PUUM | 3007 | TGG AGC ATG GGG TTC AGG (SEQ. ID NO:46) |
| Primer[b] | "HanM3004+" | TGG (TA)GC ATG GGG (CT)TC AGG (SEQ. ID NO:47) |
| PHV | 3332 | TGG TTT AAA AAG TCT GGG GAA TGG (SEQ. ID NO:48) |
| PUUM | 3335 | TGG TTT AAA AAA TCA GGT GAA TGG (SEQ. ID NO:49) |
| Primer[b] | "HanM3355-" | TGG TTT AAA AA(AG) TC(TA) GGG GAA TGG (SEQ. ID NO:50) |
| PHV | 3377 | AAT TGG ATG GTA GTG GCA GT (SEQ ID NO:51) |
| PUUM | 3380 | AAT TGG ATG GTT GTT GCT GT (SEQ ID NO:52) |
| Primer[c] | "HanM3376-" | AAT TGG ATG GT(AT) GT(GT) GCA GT (SEQ ID NO:53) |

The following primers were designed according to a similar plan, but using the S segment of PHV (GenBank X55128) or Puumala virus (GenBank M32750) as template for primer design.

were:

| PHV | 4 | TAG TAG ACT TCG TAA AGA GCT ACT A (SEQ. ID NO:54) |
|---|---|---|
| PUUM | 4 | TAG TAG ACT CCT TGA AAA GCT ACT A (SEQ. ID NO:55) |
| Primer[b] | "HanS3+" | TAG TAG ACT TCT T(AG)A A(GA)A GCT ACT A (SEQ. ID NO:56) |
| PHV | 141 | GGT GGA CCC AGA TGA CGT TAA CAA (SEQ. ID NO:57) |
| PUUM | 141 | AGT GGA CCC GGA TGA CGT TAA CAA (SEQ. ID NO:58) |
| Primer[b] | "HanS143+" | GGT GGA CCC (AG)GA TGA CGT TAA CAA (SEQ. ID NO:59) |
| PHV | 1249 | GGT GAT GAT ATG GAT CCC GAG CTA (SEQ. ID NO:60) |
| PUUM | 1249 | GGT GAT GAC ATG GAT CCT GAG CTA (SEQ. ID NO:61) |
| Primer[b,c] | "HanS1272-" | GGT GAT GA(TC) ATG GAT CCC GAG CTA (SEQ. ID NO:62) |
| PHV | 1309 | AAA GAG ATA TCT AAC CAA GAG CC (SEQ. ID NO:63) |
| PUUM | 1309 | AAA GAG ATA TCA AAC CAA GAA CC (SEQ. ID NO:64) |
| Primer[b,c] | "HanS1341-" | AAA GAG ATA TC(TA) AAC CAA GAG CC (SEQ. ID NO:65) |

In addition to the primers described above, which were all designed on the basis of sequence similarity between Prospect Hill and Puumala viruses, we designed two primers from nucleotide sequences obtained from the HARDS virus itself (the 3' portion of the 3H226 G1 1275 clone). These "HarM 1295+": GTT CAA AAA TTC AGA GGC TCA GAA (SEQ ID NO:66)

-continued
"HarM 1317+": CAA CTT CAT GTG CCA AAG AGT    (SEQ ID
                                             NO:67)

[a]The 5' end of HanMg1NT was deliberately altered from that predicted for an "ideal" primer so as to insert an Nco I restriction site (CCATGG) to allow subcloning into the PQE60 vector.
[b]"Degenerate" positions (ie, more than one nucleotide residue used in synthesis of the oligonucleotide) are indicated as parentheses [eg, "(CA)" indicates that C was incorporated into some oligonucleotide molecules, and A in others].
[c]The complement of the indicated sequence was the molecule actually synthesized (ie, antisense strand rather than sense strand).

B. Reaction Mixes and Conditions: Reverse Transcription and "First Round" PCR

The initial reaction mixes (for reverse transcription and subsequent PCR thermal cycling) were as follows. All mixtures contained 10 pmol of each primer (see Example II) (exception: MHAR G 392 reaction, which had 50 pmol of each primer); 1.7 mM 2-mercaptoethanol; 1.5 mM $MgCl_2$; 10 mM Tris-HCl (pH 8.3); 50 mM KCl; 200 μM each of DATP, dTTP, dGTP, and dCTP; 10 units of AMV reverse transcriptase (Boehringer-Mannheim), and 2.5 units of AmpliTaq™ DNA polymerase (Perkin-Elmer), in a final volume of 100 μl. After addition of all reagents to a 0.6 ml Eppendorf tube, the tubes were overlaid with 3 drops of mineral oil (Perkin-Elmer), and placed in a thermal cycler. Each tube was warmed to 42° C. for 1 h, then subjected to temperature cycling of 94°–37°–72°for 1 minute, 1 minute, and 3 or 4 minutes per cycle for 8 cycles, then 94–40–72° (1 minute, 1 minute, and 3 or 4 minutes) for 32–42 more cycles.

| | | Primers: | |
|---|---|---|---|
| Desired Product | RNA (5 μg) | Sense | Antisense |
| 3H226 S 1129 | 3H226 autopsy lung | HanS3+ | HanS1341− |
| 3H226 G1 1275 | 3H226 autopsy lung | HanM1+ | HanM1716− |
| 3H226 M 1225 | 3H226 autopsy lung | HanM1363+ | HanM2739− |
| MHAR G2 392 | MHAR autopsy lung | HanM3004+ | HanM3376− |
| 3H226 M 2038 | 3H226 autopsy lung | HarM1295+ | HanM3376− |

C. "Second Round" PCR

After the initial amplification described above, all of the samples except for the MHAR G2 392 amplification were subjected to some form of "nesting" PCR reaction, in which the amplified product was further amplified by using primers internal to those used in the first round of amplification. In the case of the 3H226 M 1225 reaction, the antisense primer was the same primer used in the first round, whereas second round amplification of 3H226 S 1129, 3H226 M 2038, and 3H226 G1 1275 were reamplified with an entirely new primer set. Fifty pmol of each "second round" primer was used; reaction ingredients included 3 μl of the first-round PCR product, and the same ingredients as those in the first round (except no 2-mercaptoethanol or reverse transcriptase was added):

| | Primers: | |
|---|---|---|
| Desired Product | Sense | Antisense |
| 3H226 S 1129 | HanS143+ | HanS1272− |
| 3H226 G1 1275 | HanMG1NT | HanM1406− |
| 3H226 M 1225 | G1P53NOI | HanM2739− |
| 3H226 M 2038 | Har M1317+ | HanM3355− |

The "second round" PCR product was prepared by thermal cycling at 94–40–72 (1 minute, 1 minute, and 3 minutes, respectively) for 8 cycles, followed by 32–38 more cycles at 94–42–72 (1 minute, 1 minute, and 3 or 4 minutes, respectively). The reaction was then subjected to an elongation step of 70° for 10 minutes. The second round DNA product (or first round, in the case of MHAR G2 392) was then loaded on an 1.2%–1.6% agarose gel, electrophoresed for 1 h at 80V, and the band of the appropriate molecular weight was then excised with a razor blade. The DNA was extracted from the gel with a glass-milk resin (Qiaex resin, Qiagen Inc.) after melting the gel in a sodium iodide solution.

D. Cloning of PCR Product and Cell Transformation

After washing the resin (according to the instructions for Qiaex resin), the PCR product was taken up in 10 μl of sterile water, and 5–10 μl was ligated to the pCRII vector according to the manufacturer's instructions (Invitrogen Corp., San Diego, Calif.). One μl of the 10 μl ligation mix was used to go transform *E. coli* cells according to the manufacturer's instructions (Invitrogen), and the transformed cells plated onto LB media containing 50 μg/ml ampicillin and 0.005% X-Gal; plates were incubated at 37° overnight. Clear colonies were selected from the plate the following morning and expanded in 4 ml of LB media containing 50 μg/ml ampicillin.

Plasmid DNA was prepared from the cultures according to standard methods, and then digested with various restriction enzymes to verify that the correct insert had been obtained. Clones that appeared to have the correct restriction enzyme digestion pattern were subjected to DNA sequencing (according to the manufacturer of the Sequenasem sequencing system, US Biochemicals) to verify that DNA with characteristics appropriate for a novel hantavirus had been amplified and cloned. Specifically, a strong homology to (but not identity to) previously-described hantaviruses Prospect Hill, Puumala, and Seoul virus, and conservation of the protein product that would be predicted from the nucleotide sequence was sought.

For use, the transformed cells are screened by conventional procedures as described above for protein production, and the products screened for desired properties.

II. Description of the Clones

The following table describes some of the characteristics of each of five exemplified clones obtained from above.

| PLASMID DESIGNATION | PRIMERS USED TO AMPLIFY DNA SEQUENCE | RESTRICTION MAP | PARTIAL INTERNAL |
|---|---|---|---|
| p3H226-S1129 CR-7 ATCC accession #75522 | 5'GGTGGACCC(AG)GATGAC GTTAACAA; (SEQ.ID NO:- 68) 5'TAGCTCGGGATCCAT(AG) TCATCACC (SEQ.ID NO:69) | EcoRI: 3.9 kb; ~.7 kb; ~.4 kb; Xba I, Xho I, Spe I, Sst I, Kpn I: 5.1 kb each | 5'AAGATGGAAG TGATTCACGGC CTCTCTTCCCCA ATGGCTCATGTAT (from 3' end of sense strand) (SEQ.ID NO:1) |
| p3H226-M2038 CR-1 ATCC accession #75532 | 5'CAACTTCATGTGCCAAAG AGT; (SEQ.ID NO:70) 5'CCATTCCCC(AT)GA(CT) TTTTTAAACCA (SEQ.ID NO:71) | Eco RI: 3.9 kb; 1.6, and 0.6 kb; HincII: 5.2 kb and 0.75 kb; Kpn I: 5.9 kb; Xho I: 4.3 kb, 1.0 kb and 0.6 kb; Pst I: 4.8 kb and 1.1 kb. | TACCAAAACTCTGGTC ATAGGCCATGTATT (from 5' end of sense strand) (SEQ.ID NO:2) |
| p3H226-M1225 CR-1 ATCC accession #75525 | 5'ACATTCTGTTTTGGCTGG; (SEQ.ID NO:72) 5'GCAAATGCACATTTCTTTCT- AAA (SEQ.ID NO:73) | Eco RI: 3.9 kb; ~0.8 kb; ~0.4 kb, Bam HI, Kpn I, Xho I 51 kb each, Sal I: uncut; Pst I: ~4.1 and ~1.1 kb. HincII: 4.4 and ~0.8 kb. | 5'GTCCTTAAGCAAT GGTGTACAACATCAT GTGTGTTTGGAGACCC CGGTGATATTGTGTCA ACGACAAGTYG (from 3' end of sense strand) (SEQ.ID NO:3) |
| pH3226-G1-1275 CR-1 ATCC accession #75524 | 5'ACCATGGAATGTCCTCAT ACTGTA; (SEQ.ID NO:74) 5'AGGGTTTTAGTAAGAAT (TG)AC(CT)TTCTT (SEQ.ID NO:75) | Eco RI: 3.9 kb, 1.3 kb Xba I, Bam HI, Xho I, Sst I, Kpn I: all 5.2 kb. | 5'GGTTTAGGTCAGGG TTACGTGACAGGTTCA GTGGAAACTACACCTA TTCTCTTAACGCAG (from 5' end of sense strand) (SEQ.ID NO:4) |
| pMHAR-G2-392 CR-1 ATCC accession #75523 | 5'TGG(TA)GCATGGGG(CT) TCAGG; (SEQ.ID NO:76) 5'ACTGC(C/A)AC(T/A) ACCATCCAATT (SEQ.ID NO:77) | Xba I, Xho I, Sal I, Sst I, Kpn I: all 4.3 kb. | GTAGGTTTCACATTGG TATGTACTGTAGGGCT AACAGAATGTGCAAAT TTTATAACTTCAAT (from 5' end of sense strand) (SEQ.ID NO:5) |

III. Serologic Immunoassay for HARDS Virus Antibodies

A. Preparation of Antibody

To raise the anti-HARDS antibodies of the invention, rDNA antigen obtained as described above in Example ID is administered to a host animal by customary routes (typically i.p., intraperitoneal) according to well-understood procedures. Host immunoglobulin is then screened for antigen-specific antibody by standard procedures, for example, by affinity chromatography with immunoadsorption of antibody on immobilized, insolubilized antigen. Alternate screening techniques include use of tracer-labelled antigen or tracer-labelled antiglobulin in standard screening immunoassays, typically including precipitation of the product immunogen-antibody complex and quantitation of associated tracer to assess antibody specificity. Of particular importance are enzyme-linked assay procedures, such as standard ELISA protocols employing an immunoreactant-linked enzyme such as peroxidase in systems including a substrate for the enzyme and dyestuff responsive to enzyme activity, radioisotope linked assays such as standard RIA protocols, and western blot immunoassays.

B. Preparation of Microtiter Plates

The wells of microtiter plates are coated with goat IgG directed against human IgM for immobilization of serum sample antibodies developed against HARDS virus.

C. Enzyme Immunoassay for HARDS Virus Antibodies

Blood samples are applied to the IgG-treated microtiter wells; the wells are then washed, and treated with purified (optionally solubilized) rDNA antigen from Example ID, above. selected for substantial specificity to HARDS virus antibodies.

After washing, the wells are treated with biotin-labelled anti-HARDS recombinant antigen rabbit antibody prepared as in A, above.

A streptavidin-conjugated alkaline phosphatase is used to detect bound biotin-labelled antibody. A chromogenic alkaline phosphatase substrate is used to detect alkaline phosphatase bound to biotin via the streptavidin moiety of the conjugate.

D. Supporting data

Serum samples were tested from four patients (2 patients who were tested within 1–7 days of admission to the hospital, i.e., "acute", and 2 who were tested 22 and 23 days after admission, and were thus "convalescent"). Their serum samples were tested for the presence of specific antibodies in Western immunoblot assays. Antigen targets present on the Western blots were bacterial fusion proteins which contained moieties encoded by the G1 and N clones of the HARDS virus. The bacterial fusion proteins were prepared from lysates of *E. coli* that contained inducible recombinant expression plasmids. The viral fusion proteins included on the Western blot membranes include (a) a protein encoded by the 1275 nt of HARDS virus G1 sequences of the clone 3H226 G1 1275 CR-1, which had been subcloned into the expression plasmid pATH 23 (Pst I-Kpn I); (b) the entire G1 protein of Puumala virus strain P360; (c) the entire N protein of Puumala virus strain P360; and (d) the protein $p37^{trp\ E}$ with no fused viral domain. After the membranes were incubated with the human serum samples, the membranes were washed and incubated with alkaline phosphatase-conjugated goat anti-human IgG (all four human sera), or goat anti-human IgM (three of the four human sera). In each case, a negative control human serum from a person who had not contracted HARDS was used to probe an replicate western blot membranes in parallel.

FIG. 4 shows the typical pattern exhibited by the antibodies of the four individuals. All four individuals' serum samples demonstrated easily detectable and specific anti-hantavirus IgG reactivity, as did all three of those who were tested for anti-hantavirus IgM. Of particular note is the observation that the G1 1275 (HARDS virus) protein reacted strongly with antibodies from all tested patients with HARDS virus infection (IgM and IgG), but the equivalent region of Puumala virus was not recognized at all by any of the four HARDS patients serum antibodies. By contrast, the N protein of Puumala virus reacted strongly with the IgG and IgM of every HARDS patient tested, which strongly supports the hypothesis that the hantavirus N proteins contain epitopes that will be recognized by antibodies directed against all related hantaviruses. The negative control serum did not recognize any virus-specific band, and no serum recognized the trp E protein expressed in the absence of a fused viral protein moiety.

It is contemplated that the insert of the clone p3H226 1129 CR-7, the HARDS virus clone that encodes the large majority of the N protein, expressed as a trp E fusion protein, will contain the epitope(s) present in the Puumala virus N protein, since the Puumala virus N protein was recognized well by HARDS is antisera, and that the HARDS virus N protein will prove to have additional or more potent epitopes when probed with anti-HARDS virus serum than Puumala virus N protein, since it is derived from homologous virus.

The nucleotide sequence (and predicted amino acid sequence) of the relevant HARDS virus clones supports the theory that the G1 gene encodes virus-specific epitopes and the N gene encodes more broadly-reactive epitopes. The HARDS virus N protein was strongly conserved (FIG. 5) between HARDS virus and its relatives Puumala and Prospect Hill virus, but large regions of the G1 protein of HARDS virus align poorly with the homologous regions of Puumala and Prospect Hill viruses (FIG. 6). In general, it can be expected that antibodies generated by exposure to divergent proteins will fail to cross-react, but that highly related proteins will tend to elicit antibodies that recognize several members of that protein group (i.e., are cross-reactive).

Section II
IV. Experimental Methods

A. Preparation of pATH23-based expression construct designed to allow Trp E-HARDS G1 protein expression (example of methods to be used to generate other expression constructs from other pCRII clones).

The clone p3H226 G1 1275 CR-1 was cut with the restriction enzymes Hind III and Xba I, and the resultant 1.3 kilobase insert was cut out of a 1% agarose gel after electrophoresis. The pATH23 vector [see Methods Enzymol. 194:477–90, 1991] was digested with the same enzymes and the digested product (~3.9 kb) was similarly purified from a gel. The 1.3 kb HARDS virus band ("insert") was mixed with the enzyme-digested vector and the Hind III and Xba I-generated ends were joined by T4 DNA ligase via standard techniques. The ligation mix was used to transform competent E. coli, strain JM101, and the bacteria were then plated onto plates containing LB media, 1.4% agarose, and 50 ug/ml ampicillin. Colonies were picked and expanded at 37° while shaking at 300 rpm in LB media containing 50 ug/ml ampicillin, and plasmid DNA isolated by standard methods. To verify that the cloning was successful, the resultant plasmid clone p3H226 G1 1275 pATH-1 was cut with restriction enzymes that would be predicted to liberate an insert of about 1300 nt and a vector band of 3.9 kb. That is what was observed.

B. Preparation of fusion proteins encoded by Puumala virus.

Molecular clones of the entire M and S segment of Puumala virus strain P360 were provided by Dr. Connie Schmaljohn of the United States Army Research Institute of Infectious Diseases in Frederick, Md. (USAMRIID). The molecular clones Dr. Schmaljohn provided were used to generate pATH expression constructs for expression of those proteins of Puumala virus that are homologous to HARDS virus clones generated. These constructs provided a means for ascertaining the degree of cross-reactivity in the immune response of people and animals infected by the HARDS virus and its relatives.

C. Induction of Trp E-G1 fusion protein expression.

The methods used to express and purify trp E-hantavirus fusion proteins are provided as an example of methods that one might use to produce large amounts of hantavirus proteins, either fused to another protein or as an unfused, native antigen. Protein expression and partial purification of the fusion protein or unfused $p37^{trp\ E}$ was carried out as described (Methods Enzymol 194:477–90). Briefly, E. coli cells (strain JM101) harboring the plasmid p3H226 G1 1275 pATH-1 were expanded in 5 ml of M9 minimal media supplemented with 1 mM $MgSO_4$, 0.1 mM $CaCl_2$, 0.2% glucose, 10 ug/ml thiamine, 50 ug/ml ampicillin, 0.5% casamino acids and 30 ug/ml of L-tryptophan. After reaching stationary phase growth, the culture was added to 45 ml of M9/casamino acids, lacking exogenous tryptophan, and grown for 1 hour at 30° with shaking at 300 rpm. At that point indoleacrylic acid was added to a final concentration of 5 ug/ml, and the induction was carried out for 4–18 hours with continued shaking at 30°. Cells were concentrated by centrifugation and suspended in 10 ml of a buffer containing 50 mM Tris-HCl (pH 8), 5 mM EDTA, and 20 mg lysozyme on ice. The suspended cells were lysed by adding the detergent triton X-100 to a final concentration of 0.8%, and NaCl was added to a final concentration of 300 mM. The insoluble protein fraction was precipitated on ice for 30 minutes, then any remaining unlysed cells were disrupted by sonication. After an additional 30 minutes of precipitation on ice, insoluble protein was pelleted by centrifugation at 16,000×g for 10 minutes. The pellet was resuspended in 0.5 ml of Laemmli buffer containing 0.5% SDS and 5% betamercaptoethanol, and rendered homogenous by sonication. The concentration of hantavirus protein was estimated by separating, via SDS-polyacrylamide gel electrophoresis, the fusion protein from contaminating bacterial products, and estimating the amount of fusion protein by visual inspection of the fusion protein band.

IV. Western Blot Assays

Approximately 5 ug of recombinant $p37^{trp\ E}$-viral fusion protein obtained as above (or $p37^{trp\ E}$ itself) was loaded per lane of a 12.5% polyacrylamide gel for SDS-PAGE. After electrophoretic separation at 200V for 45', the gel was placed into a western blot electrophoretic transfer apparatus and the proteins electrophoretically transferred onto a nitrocellulose membrane 1 hour at 4° at 100V, with the gel proteins transferred toward the cathode.

Sera for use as probe in western blot assays were preadsorbed at a concentration of 1:200 against E. coli antigens by overnight incubation at 40 in a buffer containing 20 mM Tris-HCl pH 7.5 and 0.5M NaCl ("TBS"), 1% powdered milk (Carnation), 5% lysed E. coli antigens (see below), 0.1% Triton X-100, and 0.1% deoxycholic acid. E. coli antigens were produced by induction of p37$^{trp\ E}$ in 100 ml of JM101 cells for 4 h as described above; the cells were then pelleted at 3000×g for 10 minutes and the pellet suspended in 3.6 ml of buffer containing 50 mM Tris-HCl pH 8.0, 2% SDS, and 5 mM EDTA. The cells were lysed by sonication until hot, heated in a boiling water bath for 5 minutes, and added to a final concentration of 5% in the above-mentioned preadsorption buffer. The precise contents of the preadsorption buffer, if needed, will need to be adjusted and optimized for each system of protein expression and according to the antibody specificity and immunoglobulin subtype being examined.

The membranes were placed in a tray and were pretreated by immersion in 1% powdered milk in TES wash buffer for 30 minutes at room temperature. After removing the milk buffer, the serum/preadsorption buffer was then added to the tray and incubated overnight at 4°, with rocking. In the morning, the serum/preadsorption mixture was removed and the membranes washed three times in wash buffer. An alkaline phosphatase-conjugated goat anti-human antibody directed against human IgG or IgM (diluted 1:1000 in 1% milk in TBS with or without detergents) was then used to overlay the membrane and the antihuman Ig antibody allowed to bind for 2 hours at room temperature. The membranes were then washed again three times in wash buffer, and then exposed to a substrate (nitro blue tetrazolium and BCIP) that produces a chromogenic product in the presence of alkaline phosphatase. After sufficient color development (3–20 minutes), the membranes were washed repeatedly in water to remove residual substrate.

VI. Conclusions

1. The G1-encoded protein expressed from one of the cDNA clones of the HARDS virus (p3H226 G1 1275 CR-1) contains an antigenic epitope recognizable by antibodies from patients infected with HARDS virus but not by antibodies from patients infected with closely-related hantaviruses (Puumala virus, for example).

2. The N-encoded protein of HARDS virus (clone p3H226 S 1129 CR-7) contains a broadly-reactive epitope that is recognized by human antibodies produced in response to HARDS virus infection and that also reacts with antibodies produced in response to infections with closely-related hantaviruses (Puumala virus, for example. This antigen appears to be a particularly dominant antigen for early, sensitive and specific detection of infection by the RNA HARDS virus and its relatives. It should prove to be particularly useful in detecting and characterizing infections with divergent strains of HARDS virus, particularly if antigenic variation within the G1-encoded type-specific antigen occurs among different strains.

3. The "HARDS-specific epitope" region of G1 from related hantaviruses each possess a comparable epitope that will also elicit antibodies specific to the virus eliciting the antibodies. That will also extend to new hantaviruses as they are discovered, and thus allow the development of a PCR-based method for amplifying the G1 epitope region from old or new members of the hantavirus genus, allowing extremely rapid development of type-specific diagnostic kits for new pathogens of this class.

4. The description of the G1 and N encoded proteins containing antigenic epitopes of HARDS virus provided herein permits the ready identification and isolation of viral antigens from tissue cultures infected with the virus, according to known techniques. Further, synthetic equivalents of the described proteins are easily made in a text book exercise for use as described herein, if desired.

The described epitopes identified in the G1 and N proteins of the HARDS virus appear to be determined by a very limited sequence of amino acids. It is expected that the dominant epitopes will be contained within less than 20–30 amino acids of HARDS virus sequence. According to the experience of the coinventors and that of others (working on viruses other than hantaviruses), it is expected that other hantaviruses will prove to have a type-specific epitope within the region of G1 that is homologous to that containing the type-specific epitope of the HARDS virus. A PCR system to allow the amplification, using conserved primers flanking the nucleotide sequence encoding the dominant epitope, the immunodominant region of any new hantavirus can thus be developed according to known principles.

Section III

IV. Experimental Methods

A. Amplification of HARDS Virus S Segment Nucleotide Sequence

An additional portion of the HARDS virus (HHV) S segment representing nucleotide positions 4 through 423 was cloned, producing a clone p3H226 S 419 CR-1. This clone contains the initiating ATG of the HHV N protein. The nucleotide sequence of that portion of p3H226 S 419 CR-1 that does not overlap the previous S segment clone, p3H226 S 1129 CR-7 was determined. Based upon those sequences, a PCR primer that allows the convenient amplification, subcloning and expression of the first 100 amino acids of the new clone was designed. That (sense) primer has the sequence T ACG ACT AAG CTT ATG ACG ACC CTC AAA GAA G (SEQ ID NO:78), where the bolded nucleotides make up a recognition site for the enzyme Hind III, and are followed by authentic HHV sequence, beginning with the ATG encoding the initiating methionine of N protein. For amplification and subcloning of the N-terminal 100 amino acids of HHV, an antisense primer was designed with the sequence 5' TGG TTC CTC GAG GTC AAT GGA ATT TAC ATC AAG 3'(SEQ ID NO:79). This primer was also based upon authentic HHV sequence, except that the native sequence 5' CTA GAA was replaced with the sequence CTC GAG. The complement of this palindromic sequence is bolded in the above primer sequence. CTC GAG specifies a recognition site for the restriction enzyme Xho I, but does not alter the sequence of the protein encoded by the N gene.

After amplification of p3H226 S 419 CR-1 with the above sense and antisense primers, a 317 bp product was obtained and digested with Hind III and Xho I. A plasmid derivative of pATH 23, called pATH HT-1 was also digested, with the same two enzymes. (pATH HT-1 was originally prepared by digesting pATH 23 with Xba I and Kpn I, and inserting a double-stranded oligonucleotide designed to have the "sticky ends" of Xba I and Kpn I on either side, an Xho I site, and 6 histidine codons internally.) The PCR product, now about 299 nt long after digestion, was inserted into pATH HT-1 with T4 DNA ligase. The resulting expression construct, which produces an abundant soluble protein product of about 52 kD apparent MW (AMW) upon induction, was called "p3H226 S 317 pATH-1". As discussed below, the 100 aa of HHV N protein included in the fusion protein product produced by induction harbors a potent antigenic epitope for humans infected with HARDS virus.

B. Preparation of Expression Constructs for Production of trpE-HHV N-protein Fusion Proteins An expression clone was constructed for expressing the first 407 amino acids of HHV N protein. The plasmid p3H226 S 1129 CR-7 contains coding sequence of the N protein gene that lies downstream of, but overlaps with, that of HHV clone p3H226 S 317 pATH-1. The coding sequences of p3H226 S 317 pATH-1 were joined to those of p3H226 S 1129 CR-7 to produce a larger expression construct that would allow the expression of all of the HHV N gene DNA present in a single protein molecule. To do that, a sense primer for PCR was prepared that overlapped with the antisense primer used to prepare p3H226 S 317 pATH-1. The region of overlap is the artificial Xho I site. The sense primer for amplification was thus ATT GAC CTC GAG GAA CCA AGT GGG CAA ACAG (SEQ ID NO:80). For the antisense primer, a new version of the primer originally used to generate p3H226 S 1129 CR-7 was selected. The new version of the Han S 1272-primer differed from the old primarily in that it contains a recognition site for the restriction enzyme Xba I near its 5' end: G GCT TCT AGA GGG ATC CAT GTC ATC ACC (SEQ ID NO:81).

Figure 8:
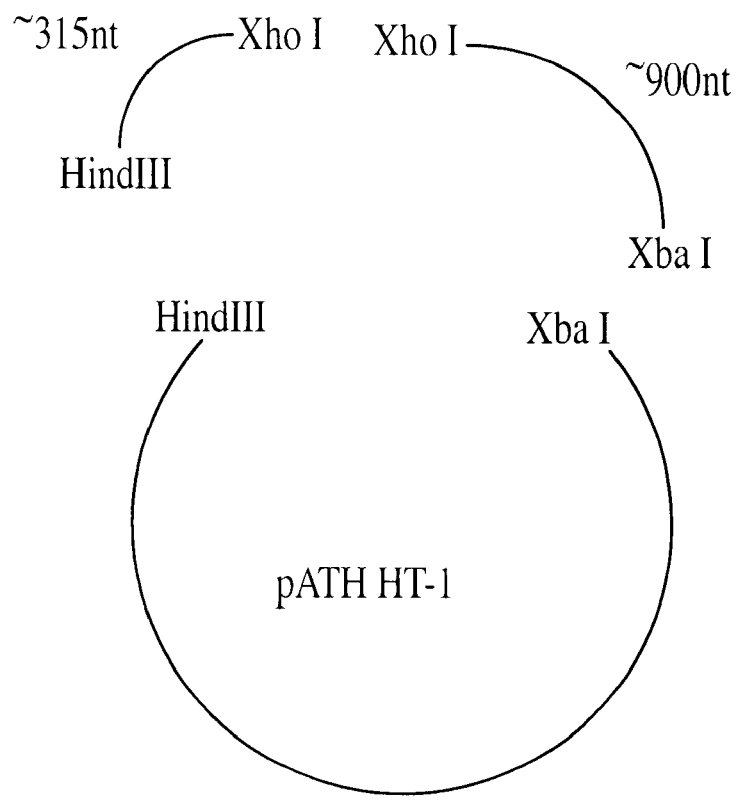
FIG. 8 illustrates the preparation of p3H226 S 1229 pATH-1 by three-way ligation.

Using p3H226 S 1129 CR-7 as template, an amplimer of about 900 bp was prepared by PCR with the above two primers. The amplimer was digested with Xho I and Xba I and was ligated to the ~299 bp Hind III/Xho I-digested amplimer described in (a) above, as well as pATH HT-1 that had been digested with Hind III and Xba I. A "three-way" ligation ensued (FIG. 8).

The resultant product was called p3H226 S 1229 pATH-7 (FIG. 10). It has been shown to have the correct restriction map, including two Xho I sites and one HindIII site spaced an appropriate distance from one another, and it produces a large amount of an insoluble trp E fusion protein of AMW ~75–78 kD after standard induction.

Expression constructs that produce other trp E-HHV N protein fusion proteins have been produced. The insert of p3H226 S 1129 CR-7 was subcloned into pATH 10 and used to produce p3H226 S 1129 pATH-1, as well as to subclone the ~750 bp Eco RI-Eco RI fragment of p3H226 S 1129 CR-7 into pATH 1 to produce p3H226 S RI pATH-1. Both of these expression constructs make large amounts of insoluble trp E-HHV N protein fusions that contain portions of the HHV N protein produced by p3H226 S 1229 pATH-7.

C. Preparation of Expression Constructs for Production of PHV Fusion Proteins

The two portions of the Prospect Hill virus (PHV) genome that correspond to the HHV sequences of clones p3H226 G1 1275 CR-1 and p3H226 S 1129 CR-7 were cloned for use in determining whether the antigenic epitopes identified within the above two HHV clones induce antibodies would cross-react with HHV's nearest relative, PHV. The PHV template was derived from a virus stock obtained as a gift from Richard Yanagihara of National Institutes of Health in July, 1993. Yanagihara's PHV stock was used to infect Vero E6 cells and PHV was propagated in the biosafety 3 facility of University of New Mexico. The PHV cDNAs were cloned from RNA prepared from those infected cultures under conditions identical to those used to clone the corresponding portions of HHV (described above). The resulting clones were called pPHV G1 1275 CR-1 and pPHV S 1129 CR-1. The PHV inserts were moved from the pCR II vector and transferred into pATH expression vectors in a manner substantially identical to that used to produce pATH expression constructs p3H226 G1 1275 pATH-1 and p3H226 S 1129 pATH-1. The expression constructs proved to be good producers of insoluble trp E fusion proteins of the appropriate size.

D. HHV G1 Epitope

The location of the dominant epitope specified by the protein product of the 1275 nt HHV G1 gene clone was determined to within 23 amino acids. The antibody response to that epitope was found to be specific to infection by HHV: serum samples from patients with HARDS do not recognize any determinant in the 1275 nt G1 protein of PHV (HARDS patients lack antibodies cross-reactive with Puumala virus G1 protein, see III D, above).

To map the epitope of HHV G1, ~20 serial exonuclease/ S1 nuclease deletions of the plasmid p3H226 G1 1275 pATH-1 were prepared, after linearization with restriction enzymes recognizing sites at the 3' end of the insert (according to the instructions of the Promega Erase-a-Bases system, Promega Corp.; see Gene 28:351–359, 1984). Each new deletion construct was induced to express its corresponding trp E-HHV G1 fusion protein. The series of fusion proteins were characterized according to their apparent MW, and a selection of proteins of various size were transferred to nitrocellulose membranes for western blot analysis. The western blot membranes were probed with serum samples from each of 2 individuals who were convalescing from HHV infection, followed by alkaline phosphatase-conjugated goat anti-human IgG. The smallest protein in the series that continued to exhibit reactivity with HARDS patient serum samples was the product of that clone that contained DNA sequences specifying amino acids 37 through 91 of G1 (using PHV M segment coordinates, beginning at the initiating methionine of PHV). Both patient serum samples were strongly reactive with that truncated protein, but lacked reactivity to the protein produced by the next largest member of the deletion series, which included amino acids 37 through 66. It was concluded from this that the epitope of the protein product of p3H226 G1 1275 pATH-1 that is recognized by patients with HHV infection lies between amino acids 66 and 91 of the G1 protein. The sequence of amino acids in that portion of the protein is SCNFDLHVPATTTQKYNQVDWTKKSS (SEQ ID NO:10). Negative control serum samples from people presumed to have had no exposure to HHV lacked reactivity to the protein product of any member of the deletion series.

Protein products of the PHV clones pPHV G1 1275 pATH-1 and pPHV S 1129 pATH-1 were tested for reactivity against the serum samples of two patients convalescing from HHV infection. Moderate reactivity to the N protein product of pPHV S 1129 pATH-1 was observed (although less brisk than that observed with the product of the HHV N gene clone p3H226 S 1129 pATH-1, ATCC #75561), but no reactivity to the product of pPHV G1 1275 pATH-1 (C, above). These results confirm the previous observation that humans infected with HHV produce antibodies to the HHV G1 protein that do not cross-react with other hantaviruses (Puumala virus and PHV). Thus, the HHV G1 protein epitope described is HHV antibody-specific and highly useful for differentiation of antibodies responsive to HIV infection from antibodies responsive to PHV infection, Puumala virus infection, or infection by other hantaviruses yet to be identified.

E. HHV N-protein Epitopes—Expression Constructs and Antigen Activity

At least two independent epitopes of HHV N protein, which can be used independently in serologic assays for HHV infection in man have been identified. Four plasmid constructs designed to express different domains of HHV N protein were produced as described above. An additional clone, not described above, spans only the 3' 262 nt of the insert and 3' PCR primer of p3H226 S 1129 CR-7, and is called p3H226 S 238 pATH-1. The following Table describes characteristics of five clones:

| Clone name | Fusion Protein (AMW) | PHV Coordinates (nt/aa) |
|---|---|---|
| p3H226 S 1229 pATH-7 | ~78 kD | 43-1272/1-407 |
| p3H226 S 317 pATH-1 | ~52 kD | 43-343/1-100 |
| p3H226 S 238 pATH-1 | ~45 kD | 1008-1272/322-407 |
| p3H226 S RI pATH-1 | ~60 kD | 509-1272/155-407 |
| p3H226 S 1129 pATH-1 | ~75 kD | 141-1272/34-407 |

Fusion proteins were produced in large amounts from each of these constructs, and used in western blot format to detect serum IgG antibodies from patients with HARDS. For each of 8 serum samples from patients with acute (5) or convalescent (3) HHV infection, intense and specific seroreactivity was demonstrated against the 52 kD product of p3H226 S 317 pATH-1 and the 78 kD product of p3H226 S 1229 pATH-7, but not against the 45 kD product of p3H226 S 238 pATH-1. All HHV/HARDS sera tested were also active against the intact Puumala N protein, but at diminished intensity compared to the proteins encoded by authentic HHV N gene clones. A negative control serum from a normal blood donor did not recognize any of the recombinant fusion proteins, and no serum reacted with $p37^{trp\ E}$ lacking an HHV fusion moiety. These studies showed that the first 407 amino acids of HHV N protein contain at least one potent epitope, and that at least one of those epitope(s) is present in the first 100 amino acids. No epitopes were judged to be present in amino acids 322–407.

A second experiment examined the reactivity of proteins expressed by all of the above constructs (except for p3H226 S 238 pATH-1, which did not appear to encode any significant epitopes), using as probe convalescent serum samples from two patients with HHV-HARDS. The intense and specific reactivity to amino acids 1–407 was again observed, as was intense reactivity to amino acids 1–100. Significantly, moderate IgG seroreactivity with both was also observed in the products of p3H226 S RI pATH-1 and p3H226 S 1129 pATH-1. The reactivity of the product of p3H226 S RI pATH-1 was significant because that construct has no sequences overlapping with those of p3H226 S 317 pATH-1, where a dominant antigenic determinant had already been localized. A negative control serum again failed to recognize any fusion protein, and no serum recognized $p37^{trp\ E}$ lacking an HHV fusion moiety. These experiments demonstrate that infected patients react to at least 2 specific epitopes of HHV N protein. One such epitope is localized within the first 100 amino acids, and the other is subtended by amino acids 155 through 407. Based upon the lack of antigenic activity of the protein coordinates 322–407, it appears that the epitope(s) between 155–407 lies between amino acids 155 and 321. The identification of the second epitope of N (between aa 155 and 321) allows for the development of a "3-antigen" recombinant diagnostic system that should be an improvement over our previously-described 2-antigen western blot.

F. Detection of HARDS Virus Antibodies

The 2-antigen recombinant western blot assay developed (and described previously) is used for detecting serum IgG or IgM antibodies from patients infected with HHV, even in the earliest stage of infection, and reliably diagnose acute HHV infection. In a blinded study of 30 serum samples, of which 20 were derived from control patients who were presumably never exposed to HHV, and of which 10 came from 8 patients with HHV infection, manifested as HARDS. Using alkaline phosphatase-conjugated goat anti-human IgG or -IgM as secondary antibody, bound antibodies were detected from all 10 samples from patients with HARDS (reactive with both HHV G1 and Puumala virus N protein). All 10 patients had reactivity to both antigens with IgG; 9 of the 10 had reactivity to both antigens with IgM. Of the controls, one demonstrated IgG reactivity to Puumala N protein in isolation; s/he was labeled "indeterminate" and correctly identified as uninfected. Although the blinded study was conducted with N protein derived from Puumala virus, subsequent data prove convincingly that HHV N protein reacts even more intensely with serum samples from patients with HHV infection than does Puumala N protein, and will prove to be a more sensitive indicator of HHV infection.

Section IV

Serum samples from 31 patients in the acute stage of HARDS (all within 2–3d of admission to the hospital, or, in the case of 7 patients, their death and subsequent autopsy) were tested. All samples had IgM and IgG reactivity by Western blot with that portion of the HARDS virus N protein encoded by clones p3H226 S 1229 pATH-7 and p3H226 S 317 pATH-1. 31 of the 31 and 26 of the 31 had IgG or IgM reactivity, respectively, with the protein encoded by the G1 protein expression construct p3H226 G1 1275 pATH-1. The dominant epitope of the FCV N protein appears to be contained within the first 110 amino acids.

A. Determination that one or more epitopes encoded by the clone p3H226 S 317 pATH-1 are cross-reactive with a homologous portion (ie, the first 110 amino acids) of the Prospect Hill virus (PHV) N protein.

That portion of the PHV N protein gene was cloned by reverse transcriptase PCR as above, using RNA prepared from PHV-infected Vero cell cultures. The sense primer for PHV was synthesized specifically for amplification of PHV cDNA and had the sequence T ACT ACA GTC GAC GGG ATG AGC CAA CTC AGG GA (SEQ ID NO:82). The antisense primer was the same as that used above to amplify the corresponding portion of FCV cDNA and had the sequence TGG TTC CTC GAG GTC AAT GGA ATT TAC ATC AAG (SEQ ID NO:83). The amplified DNA was gel-purified and digested with the restriction enzymes Sal I and Xho I (recognition sites for which are present in the above primers) and cloned directly into Sal I- and Xho I-digested pATH HT-1. The resulting construct was called pPHV S 317 pATH-1.

Trp E fusion protein was expressed from pPHV S 317 pATH-1 obtained from PHV according to standard protocol. Soluble protein was compared to that expressed from p3H226 S 317 pATH-1 according to the invention, and subjected to Western blot analysis using 8 serum samples from patients with HARDS as the source of antibodies. Both the FCV and PHV proteins were reactive with all 8 HARDS serum samples.

Conclusion: A dominant epitope contained within the first 110 amino acids of FCV is cross-reactive with its PHV homolog.

B. Location of the dominant epitope of N protein encoded by the plasmid clone p3H226 S 317 pATH-1.

Mapping was accomplished by producing a nested set of 3' and 5' deletions of the DNA insert of this clone and expressing the truncated insert as protein (*Gene* 28:351–359). FIG. 12 shows a Western blot produced by reacting trp E fusion proteins expressed from various members of a nested deletion series with serum (1:200 dilution) from two patient with HARDS (panels A and B) or an uninfected control (panel C). This deletion series was produced by linearizing the p3H226 S 317 pATH-1 plasmid in the polylinker sequence lying 3' of the FCV nucleocapsid gene insert and digesting the 3' end of the viral cDNA to varying extents with exonuclease III. A series of proteins were produced that had sustained larger and larger C-terminal deletions, and were thus smaller and smaller in size. Several members of the deletion series were reactive with serum samples from all 5 HARDS patients tested. The smallest protein that continued to be reactive with the 5 HARDS serum samples contained amino acids 1 through 59 of the FCV N protein. By contrast, the next smallest member of the N protein deletion series failed to react with any HARDS patient serum sample. The nucleotide sequence of that clone showed that it encoded amino acids 1 through 41 of FCV N protein. These studies showed that the carboxy terminus of the dominant epitope of FCV N protein lies between amino acids 41 and 59.

The amino terminus of the epitope was mapped by preparing an amino-terminal deletion series from p3H226 S 317 pATH-1. This series was constructed by synthesizing selected sense primers designed to allow PCR amplification of DNAs from a p3H226 S 317 pATH-1 template, using the same antisense primer that was originally used to make p3H226 S 317 pATH-1. The sense primers were designed so that pATH HT-1 subclones prepared from the amplified DNA would encode in-frame trp E fusion proteins lacking varying amounts of the amino-terminus of the N protein.

For two of the five HPS serum samples tested, FCV N IgG antibodies reacted with the amino-to-carboxy terminus deletion construct p3H226-S-NEx91 (aa17-aa110) and did not react with p3H226-S-CEx136 (aa32-aa110). These reactivities placed the amino terminus boundary of the epitope between aa17 and aa32. For these two serum samples, the epitope mapping data indicate that an epitope is present between FCV N aa17 and aa59. The amino acid sequence of this segment is QLVTARQKLKDARRAVELDPDDVNK-STLQSRRAAVSALETKLG (SEQ ID NO:6). The sequences of the corresponding portion of PHV and Puumala virus N proteins is QLVIARQKLKEAERTVEVDPD-DVNKSTLQSRRSAVSTLEDKLA (SEQ ID NO:7) and QLVVARQKLKDAERAVEVYPD-DVNKNTLQARQQTVSALEDKLA (SEQ ID NO:8). For the other three HPS serum samples tested, antibody reactivity was observed to all of the amino-to-carboxy terminal deletion clones that were tested (extending to aa60). These reactivities indicate that the N segment in p3H226-S-330 contains a second antibody-reactive epitope that is located closer to the carboxy terminus relative to the epitope between aa17 and aa59. aa17 and aa59 may be a dominant epitope that is responsible for the cross-reactivity of FCV N antibodies with PHV N and Puumala virus N proteins.

C. Seroreactivity to the dominant epitope of FCV N protein.

Reactivity is specific for FCV infection. Serum samples obtained from 128 control subjects were tested for IgG antibody reactivities to the FCV N and G1 proteins. In contrast to the HPS cases above, only one of the control serum samples (0.8%) contained antibodies to both the FCV N and FCV G1 recombinant proteins. Nine of 128 control serum samples (7%) contained antibodies that reacted with the FCV N protein. The N antibody reactivities present among the control subjects mapped to an antigen site that was different from the epitope recognized by confirmed FCV-induced antibodies. Therefore, it unlikely that the N reactivities present among controls resulted from remote unrecognized FCV infections. These N reactivities may represent cross-reactive antibodies induced by infection with a different, perhaps uncharacterized, hantavirus. It is more likely that they represent antibodies induced by an irrelevant antigen that fortuitously cross-reacts with an epitope in the FCV N protein. The observation that these antibodies recognize an epitope that is different from the dominant N epitope recognized by FCV-induced antibodies provides a means for differentiating true positive FCV N antibody reactivities from false positive reactivities.

D. G1 Protein Mapping

The location of the carboxy-terminal boundary of the dominant epitope specified by the protein product of the 1275 nt FCV G1 gene clone has been determined to within 23 amino acids. The carboxy terminus of the epitope was mapped by preparing a nested series of deletions of the 3' end of the FCV insert of p3H226 G1 1275 pATH-1. A similar approach was used to prepare a series of 5' deletions of the p3H226 G1 1275 pATH-1 insert. The latter series was prepared to allow the mapping of the amino-terminal boundary of the G1 protein epitope. FCV G1-reactive antibodies reacted with the p3H226-M-NEx222 protein (aa59-aa452) and did not react with the p3H226-M-NEx 297 protein (aa84-aa452).

All amino-to-carboxy terminus deletion constructs that were deleted beyond amino acid coordinate 84 did not react with the FCV G2-reactive antibodies. Therefore, the amino terminus boundary of the type-specific epitope(s) lies between amino acid coordinates 59 and 84. Taken in conjunction with the mapping data from the carboxy-terminal deletion series presented above, G1 immunoreactivity was localized to a single segment between aa59 and aa89 (the amino acid sequence coordinates are given in terms of the homologous positions in the sequence of Prospect Hill virus) This polypeptide segment has the amino acid sequence LKIESSDNFDLHVPATTTQKYNQVDWTKKSS (SEQ ID NO:9). This sequence is divergent from the homologous regions of Prospect Hill virus (LKLSSCNFDVHTSSATQQAVTKWTWEKKAD) (SEQ ID NO:84) and Puumala virus (LKLESSCNFDLHTSTAGQQSFTKWTWEIKGD) (SEQ ID NO:85). The degree of amino acid sequence variation within this segment is consistent with the observation that FCV G1-reactive antibodies fail to cross-react with homologous regions of the G1 proteins of PHV and Puumala virus.

In the following claims, the term "protein" includes protein fragments (oligopeptides). The claimed sequences include sequences with variations or modifications which do not substantially adversely affect the properties of the products for their intended use. Artifacts of peptide synthesis are exemplary.

The coordinates given in the claims are PHV coordinates beginning at the initiating methionine of PHV.

(Under the terms of the Budapest Treaty on the International Recognition of the Deposit of Microorganisms for the Purpose of Patent Procedure, deposits of plasmid 3H226-S1129 CR-7, plasmid 3H226-M2038 CR-1, plasmid 3H226-M1225 CR-1, plasmid 3H226-G1-1275 CR-1, plasmid MHAR-G2-392 CR-1, and plasmid 3H226-S1229-pATH-1 were made with the American Type Culture Collection (ATCC) of Rockville, Md., USA, where the deposits were given ATCC Accession Numbers #75522, #75532, #75525, #75524, #75523, and #75561, respectively.

Applicant's assignee, the University of New Mexico, represents that the ATCC is a depository afforded permanence of the deposit and ready accessibility thereto by the public if a patent is granted. All restrictions on the availability to the public of the material so deposited will be irrevocably removed upon granting of a patent. The material will be readily available during the pendency of the patent application to one determined by the Commissioner to be entitled thereto under 37 C.F.R. §1.14 and 35 U.S.C. §122. The deposited material will be maintained with all the care necessary to keep it viable and uncontaminated for a period of at least five years after the most recent request for the furnishing of a sample of the deposited material, and in any case, for a period of at least thirty (30) years after the date of the deposit or for the enforceable life of the patent, whichever period is longer. Applicant's assignee acknowledges its duty to replace the deposit should the depository be unable to furnish a sample when requested due to the condition of the deposit.)

```

What is claimed is:

1. A cDNA insert comprising an expression vector containing recombinant DNA (rDNA) wherein said rDNA consists of a coding sequence of Hantavirus-Associated Respiratory Distress Syndrome virus, said coding sequence being selected from the group consisting of an isolated nucleic acid encoding HARDS virus M segment (SEQ ID NO:23) and an isolated nucleic acid encoding HARDS virus S segment (SEQ ID NO:20).

2. A cDNA insert comprising an expression vector selected from the group consisting of plasmid 3H226-S1129 CR-7 (ATCC #75522), plasmid 3H226-M2038 CR-1 (ATCC #75532), plasmid 3H226-M1225 CR-1 (ATCC #75525), plasmid 3H226-G1-1275 CR-1 (ATCC #75524), plasmid MHAR-G2-392 CR-1 (ATCC #75523), and plasmid 3H226-S1229-pATH-1 (ATCC #75561).

3. A transformed or transfected host cell expressing recombinant DNA (rDNA) wherein said rDNA consists of a BARDS virus genome segment selected from the group consisting of an isolated HARDS virus M segment (SEQ ID NO:23) and an isolated HARDS virus S segment (SEQ ID NO:20).

4. A molecular clone including an expression vector containing recombinant DNA encoding a HARDS virus antigenic protein or polypeptide wherein said protein or polypeptide is encoded by a nucleic acid selected from the group consisting of an isolated HARDS virus M segment consisting of the sequence SEQ ID NO:23 and an isolated HARDS virus S segment consisting of the sequence SEQ ID NO:20.

5. Recombinant DNA (rDNA) encoding a HARDS virus antigenic protein or polypeptide wherein said protein or polypeptide is encoded by an isolated nucleic acid selected from the group consisting of an isolated nucleic acid consisting of the HARDS virus M segment consisting of the sequence (SEQ ID NO:23) and an isolated nucleic acid consisting of the HARDS virus S segment consisting of the sequence (SEQ ID NO:20).

6. rDNA according to claim 5, wherein said isolated nucleic acid consists of the nucleotide sequence SEQ ID NO:23.

7. rDNA encoding a HARDS virus antigenic protein or polypeptide wherein said protein or polypeptide is encoded by an isolated nucleic acid consisting of the HARDS virus glycoprotein G1 coding sequence of SEQ ID NO:23.

8. rDNA encoding a HARDS virus antigenic protein or polypeptide, wherein said protein or polypeptide is encoded by an isolated nucleic acid consisting of the sequence of SEQ ID NO:23 that encodes amino acids 59 to 89 of the HARDS virus glycoprotein G1 protein, referenced to the amino acid sequence of Prospect Hill Virus (PHV).

9. rDNA encoding a HARDS virus antigenic protein or polypeptide, wherein said protein or polypeptide is encoded by an isolated nucleic acid consisting of the sequence of SEQ ID NO:23 that encodes the amino acid sequence SCNFDLHVPATTTQKYNQVDWTKKSS (SEQ ID NO:10).

10. rDNA encoding a HARDS virus antigenic protein or polypeptide, wherein said protein or polypeptide is encoded by an isolated nucleic acid consisting of the HARDS virus nucleocapsid (N) protein coding sequence of the HARDS virus S segment that encodes a polypeptide consisting of amino acids 1 to 407, referenced to the amino acid sequence of Prospect Hill Virus (PHV).

11. rDNA encoding a HARDS virus antigenic protein or polypeptide, wherein said protein or polypeptide is encoded by an isolated nucleic acid consisting of the HARDS virus nucleocapsid (N) protein coding sequence of the HARDS virus S segment, wherein said N protein coding sequence encodes a polypeptide consisting of amino acids 153 to 321, referenced to the amino acid sequence of Prospect Hill Virus (PHV).

12. rDNA encoding a HARDS virus antigenic protein or polypeptide, wherein said protein or polypeptide is encoded by an isolated nucleic acid consisting of the HARDS virus nucleocapsid (N) protein coding sequence of the HARDS virus S segment, wherein said N protein coding sequence encodes a polypeptide consisting of amino acids 1 to 100, referenced to the amino acid sequence of PHV.

13. rDNA encoding a HARDS virus antigenic protein or polypeptide, wherein said protein or polypeptide is encoded by an isolated nucleic acid consisting of the HARDS virus nucleocapsid (N) protein coding sequence of the HARDS virus S segment, wherein said N protein coding sequence encodes a polypeptide consisting of amino acids 17 to 59, referenced to the amino acid sequence of PHV.

* * * * *

                         SEQUENCE LISTING

<160> NUMBER OF SEQ ID NOS:  90

<210> SEQ ID NO 1
<211> LENGTH: 46
<212> TYPE: DNA
<213> ORGANISM: Four Corners hantavirus

<400> SEQUENCE: 1
aagatggaag tgattcacgg cctctcttcc ccaatggctc atgtat              46

<210> SEQ ID NO 2
<211> LENGTH: 30
<212> TYPE: DNA
<213> ORGANISM: Four Corners hantavirus

<400> SEQUENCE: 2
taccaaaact ctggtcatag gccatgtatt                                30

<210> SEQ ID NO 3
<211> LENGTH: 70
<212> TYPE: DNA
<213> ORGANISM: Four Corners hantavirus

<400> SEQUENCE: 3
gtccttaagc aatggtgtac aacatcatgt gtgtttggag accccggtga tattgtgtca 60
acgacaagtg                                                      70

<210> SEQ ID NO 4
<211> LENGTH: 60
<212> TYPE: DNA
<213> ORGANISM: Four Corners hantavirus

<400> SEQUENCE: 4
ggtttaggtc agggttacgt gacaggttca gtggaaacta cacctattct cttaacgcag 60

<210> SEQ ID NO 5
<211> LENGTH: 62
<212> TYPE: DNA
<213> ORGANISM: Four Corners hantavirus

<400> SEQUENCE: 5
gtaggtttca cattggtatg tactgtaggg ctaacagaat gtgcaaattt tataacttca 60
at                                                              62

<210> SEQ ID NO 6
<211> LENGTH: 43
<212> TYPE: PRT
<213> ORGANISM: Four Corners hantavirus

<400> SEQUENCE: 6

Gln Leu Val Thr Ala Arg Gln Lys Leu Lys Asp Ala Glu Arg Ala Val
  1               5                  10                  15
```

-continued

Glu Leu Asp Pro Asp Asp Val Asn Lys Ser Thr Leu Gln Ser Arg Arg
           20                    25                   30

Ala Ala Val Ser Ala Leu Gly Thr Lys Leu Gly
          35                   40

<210> SEQ ID NO 7
<211> LENGTH: 43
<212> TYPE: PRT
<213> ORGANISM: Prospect Hill virus

<400> SEQUENCE: 7

Gln Leu Val Ile Ala Arg Gln Lys Leu Lys Glu Ala Glu Arg Thr Val
1             5                  10                 15

Glu Val Asp Pro Asp Asp Val Asn Lys Ser Thr Leu Gln Ser Arg Arg
          20                   25                 30

Ser Ala Val Ser Thr Leu Glu Asp Lys Leu Ala
          35                 40

<210> SEQ ID NO 8
<211> LENGTH: 43
<212> TYPE: PRT
<213> ORGANISM: Puumala virus

<400> SEQUENCE: 8

Gln Leu Val Val Ala Arg Gln Lys Leu Lys Asp Ala Glu Arg Ala Val
1             5                  10                 15

Glu Val Tyr Pro Asp Asp Val Asn Lys Asn Thr Leu Gln Ala Arg Gln
          20                   25                 30

Gln Thr Val Ser Ala Leu Glu Asp Lys Leu Ala
          35                 40

<210> SEQ ID NO 9
<211> LENGTH: 31
<212> TYPE: PRT
<213> ORGANISM: Four Corners hantavirus

<400> SEQUENCE: 9

Leu Lys Ile Glu Ser Ser Asp Asn Phe Asp Leu His Val Pro Ala Thr
1             5                  10                 15

Thr Thr Gln Lys Tyr Asn Gln Val Asp Trp Thr Lys Lys Ser Ser
          20                   25                 30

<210> SEQ ID NO 10
<211> LENGTH: 26
<212> TYPE: PRT
<213> ORGANISM: Four Corners hantavirus

<400> SEQUENCE: 10

Ser Cys Asn Phe Asp Leu His Val Pro Ala Thr Thr Thr Gln Lys Tyr
1             5                  10                 15

Asn Gln Val Asp Trp Thr Lys Lys Ser Ser
          20                   25

<210> SEQ ID NO 11
<211> LENGTH: 31
<212> TYPE: PRT
<213> ORGANISM: Four Corners hantavirus

<400> SEQUENCE: 11

Leu Lys Ile Glu Ser Ser Asp Asn Phe Asp Leu His Val Pro Ala Thr
1             5                  10                 15

```
Thr Thr Gln Lys Tyr Asn Gln Val Asp Trp Thr Lys Lys Ser Ser
            20                  25                  30
```

<210> SEQ ID NO 12
<211> LENGTH: 26
<212> TYPE: PRT
<213> ORGANISM: Four Corners hantavirus

<400> SEQUENCE: 12

```
Ser Cys Asn Phe Asp Leu His Val Pro Ala Thr Thr Thr Gln Lys Tyr
 1               5                  10                  15

Asn Gln Val Asp Trp Thr Lys Lys Ser Ser
            20                  25
```

<210> SEQ ID NO 13
<211> LENGTH: 76
<212> TYPE: DNA
<213> ORGANISM: Four Corners hantavirus

<400> SEQUENCE: 13

```
tcttgtaatt tcgatctgca tgtcccggct actactaccc aaaaatacaa tcaggttgac      60
tggaccaaaa aaagtt                                                     76
```

<210> SEQ ID NO 14
<211> LENGTH: 26
<212> TYPE: PRT
<213> ORGANISM: Four Corners hantavirus

<400> SEQUENCE: 14

```
Ser Cys Asn Phe Asp Leu His Val Pro Ala Thr Thr Thr Gln Lys Tyr
 1               5                  10                  15

Asn Gln Val Asp Trp Thr Lys Lys Ser Ser
            20                  25
```

<210> SEQ ID NO 15
<211> LENGTH: 70
<212> TYPE: PRT
<213> ORGANISM: Four Corners hantavirus

<400> SEQUENCE: 15

```
Met Ser Thr Leu Lys Glu Val Gln Asp Asn Ile Thr Leu His Glu Gln
 1               5                  10                  15

Gln Leu Val Thr Ala Arg Gln Lys Leu Lys Asp Ala Glu Arg Ala Val
            20                  25                  30

Glu Leu Asp Pro Asp Asp Val Asn Lys Ser Thr Leu Gln Ser Arg Arg
        35                  40                  45

Ala Ala Val Ser Ala Leu Glu Thr Lys Leu Gly Glu Leu Lys Arg Glu
    50                  55                  60

Leu Ala Asp Leu Ile Ala
 65                  70
```

<210> SEQ ID NO 16
<211> LENGTH: 43
<212> TYPE: PRT
<213> ORGANISM: Four Corners hantavirus

<400> SEQUENCE: 16

```
Gln Leu Val Thr Ala Arg Gln Lys Leu Lys Asp Ala Glu Arg Ala Val
 1               5                  10                  15

Glu Leu Asp Pro Asp Asp Val Asn Lys Ser Thr Leu Gln Ser Arg Arg
            20                  25                  30
```

Ala Ala Val Ser Ala Leu Glu Thr Lys Leu Gly
         35                  40

<210> SEQ ID NO 17
<211> LENGTH: 1008
<212> TYPE: DNA
<213> ORGANISM: Four Corners hantavirus

<400> SEQUENCE: 17

| | | | | | |
|---|---|---|---|---|---|
| agcacattac | agagcagacg | ggcagctgtg | tctgcattgg | agaccaaact | cggagaactc | 60 |
| acagggattg | aacctgatga | ccatttaaag | gaaaaatcat | cactgagata | tggaaatgtc | 120 |
| cttgatgtaa | attccattga | cctagaagaa | ccaagtgggc | aaacagctga | ttggaaatcc | 180 |
| atcggactct | acattctaag | ttttgcatta | ccgattatcc | ttaaagcctt | gtacatgtta | 240 |
| tctactagag | gccgtcaaac | aatcaaagaa | acaagggaa | caagaattcg | atttaaggat | 300 |
| gattcatctt | atgaagaagt | caatggaata | cgtaaaccaa | gacatctata | tgtttctatg | 360 |
| ccaactgctc | agtctacaat | gaaagcagat | gagattactc | ctgggaggtt | ccgtacaatt | 420 |
| gcttgtgggt | tattcccggc | ccaagtcaaa | gcaaggaata | ttatcagtcc | tgttatgggt | 480 |
| gtgattggct | ttagtttctt | tgtgaaagat | tggatggaaa | gaattgatga | ctttctggct | 540 |
| gcacgttgtc | catttctacc | cgaacagaaa | gaccctaggg | atgctgcatt | ggcaactaac | 600 |
| agagcctatt | ttataacacg | tcaattacag | gttgatgagt | caaaggttag | tgatattgag | 660 |
| gatctaattg | ctgatgcaag | ggctgagtct | gccactatat | tcgcagatat | cgccactcct | 720 |
| cattcagttt | gggtcttcgc | atgtgctcca | gatcgttgtc | cacctacagc | attatatgtg | 780 |
| gccgggatgc | cggagttggg | tgcatttttt | gctattcttc | aggatatgag | gaacaccata | 840 |
| atggcatcaa | aatctgtggg | gacatctgaa | gagaaattga | agaaaaaatc | agcattctac | 900 |
| cagtcatact | tgagacgtac | tcagtcaatg | gggattcaac | tggaccagaa | gataatcatc | 960 |
| ttatacatga | gccattgggg | aagagaggcc | gtcaatcact | tccatcttt | | 1008 |

<210> SEQ ID NO 18
<211> LENGTH: 1224
<212> TYPE: DNA
<213> ORGANISM: Four Corners hantavirus

<400> SEQUENCE: 18

| | | | | | |
|---|---|---|---|---|---|
| ggtttagctc | agggttacgt | gacaggttca | gtggaaacta | cacctattct | cttaacgcag | 60 |
| gtagctgatc | ttaagattga | gagttcttgt | aatttcgatc | tgcatgtccc | ggctactact | 120 |
| acccaaaaat | acaatcaggt | tgactggacc | aaaaaaagtt | caactacaga | agcacaaat | 180 |
| gcaggtgcaa | ctacatttga | ggctaaaaca | aaagagataa | atttaaaagg | cacatgtaat | 240 |
| attcttccaa | ctcatttga | agctgcatat | aaatcaagga | agacagtaat | ttgttatgat | 300 |
| ttagcctgta | atcaaacaca | ttgtcttcct | acagtccatt | tgattgctcc | tgttcaaacg | 360 |
| tgcatgtctg | tgcggagctg | tatgataggt | ttgctgtcaa | acaggattca | agtcatatat | 420 |
| gagaagacat | actgtgttac | aggtcaatta | atagaggggc | tatgtttcat | cccaacacat | 480 |
| acaattgcac | tcacacaacc | tggtcatacc | tatgatacta | tgacattgcc | agtgacttgt | 540 |
| tttttagtag | ctaaaaagtt | gggaacacaa | cttaagctgg | ctgttgagtt | agagaaactg | 600 |
| attactggtg | tgagttgcac | agaaaacagc | tttcaaggtt | actacatctg | ctttatcgga | 660 |
| aaacattcag | agcccttatt | tgtgccaaca | atggaagatt | ataggtcagc | tgagttattt | 720 |
| acccgtatgg | ttttaaatcc | gagaggtgaa | gatcatgacc | ctgatcaaaa | tggacaaggc | 780 |

```
ttaatgagaa tagccggacc tgttacagct aaggtgccat ctacagaaac tggacaaggc       840
atgcaaggaa ttgcatttgc tggggcaccg atgtatagct ctttctcaac tctcgtgagg       900
aaggctgatc ctgagtatgt cttctcccca ggtataattg cagaatcaaa tcatagtgtc       960
tgtgataaga aaacagtacc ccttacatgg acagggtttt tggcagtttc tggagagata      1020
gagaaaataa caggctgtac agtcttctgt acattggcag gacctggtgc tagttgtgaa      1080
gcatactcag aaacaggaat ctttaatata aacttcatgt gccaaagagt gaataaagtt      1140
caaaaattca gaggctcaga acagagaatc aacttcatgt gccaaagagt tgatcaagat      1200
gttgtagtct attgtaatgg gcaa                                             1224

<210> SEQ ID NO 19
<211> LENGTH: 76
<212> TYPE: DNA
<213> ORGANISM: Four Corners hantavirus

<400> SEQUENCE: 19
tcttgtaatt tcgatctgca gtcccggct actactaccc aaaaatacaa tcaggttgac         60
tggaccaaaa aaagtt                                                        76

<210> SEQ ID NO 20
<211> LENGTH: 1191
<212> TYPE: DNA
<213> ORGANISM: Four Corners hantavirus

<400> SEQUENCE: 20
atgagcaccc tcaaagaagt gcaagacaac attactctcc acgaacaaca acttgtgact        60
gccaggcaga agctcaaaga tgcagaaaga gcggtggaat tggaccccga tgatgttaac       120
aaaagcacat tacagagcag acgggcagct gtgtctgcat tggagaccaa actcggagaa       180
ctcaagcggg aactggctga tcttattgca gctcagaaat tggcttcaaa acctgttgat       240
ccaacaggga ttgaacctga tgaccattta aaggaaaaat catcactgag atatggaaat       300
gtccttgatg taaattccat tgacctcgag gaaccaagtg ggcaaacagc tgattggaaa       360
tccatcggac tctacattct aagttttgca ttaccgatta ccttaaagc cttgtacatg       420 ttatctacta gaggccgtca acaatcaaa gaaacaagg gaacaagaat tcgatttaag       480
gatgattcat cttatgaaga agtcaatgga atacgtaaac caagacatct atatgtttct       540
atgccaactg ctcagtctac aatgaaagca gatgagatta ctcctgggag gttccgtaca       600
attgcttgtg ggttattccc ggcccaagtc aaagcaagga atattatcag tcctgttatg       660
ggtgtgattg gctttagttt ctttgtgaaa gattggatgg aaagaattga tgactttctg       720
gctgcacgtt gtccattcct acccgaacag aaagacccta gggatgctgc attggcaact       780
aacagagcct attttataac acgtcaatta caggttgatg agtcaaaggt tagtgatatt       840
gaggatctaa ttgctgatgc aagggctgag tctgccacta tattcgcaga tatcgccact       900
cctcattcag tttgggtctt cgcatgtgct ccagatcgtt gtccacctac agcattatat       960
gtggccggga tgccggagtt gggtgcattt tttgctattc ttcaggatat gaggaacacc      1020
ataatggcat caaatctgt gggacatctc aagagaaat tgaagaaaaa atcagcattc       1080
taccagtcat acttgagacg tactcagtca atggggattc aactggacca gaagataatc      1140
atcttataca tgagccattg gggaagagag gccgtgaatc acttccatct t              1191

<210> SEQ ID NO 21
```

```
<211> LENGTH: 330
<212> TYPE: DNA
<213> ORGANISM: Four Corners hantavirus

<400> SEQUENCE: 21
atgagcaccc tcaaagaagt gcaagacaac attactctcc acgaacaaca acttgtgact      60
gccaggcaga agctcaaaga tgcagaaaga gcggtggaat tggaccccga tgatgttaac     120
aaaagcacat tacagagcag acgggcagct gtgtctgcat tggagaccaa actcggagaa     180
ctcaagcggg aactggctga tcttattgca gctcagaaat tggcttcaaa acctgttgat     240
ccaacaggga ttgaacctga tgaccattta aaggaaaaat catcactgag atatggaaat     300
gtccttgatg taaattccat tgacctcgag                                      330

<210> SEQ ID NO 22
<211> LENGTH: 109
<212> TYPE: PRT
<213> ORGANISM: Four Corners hantavirus

<400> SEQUENCE: 22

Met Ser Thr Leu Lys Glu Val Gln Asp Asn Ile Thr Leu His Glu Gln
 1               5                  10                  15

Gln Leu Val Thr Ala Arg Gln Lys Leu Lys Asp Ala Glu Arg Ala Val
            20                  25                  30

Glu Leu Asp Pro Asp Asp Val Asn Lys Ser Thr Leu Gln Ser Arg Arg
        35                  40                  45

Ala Ala Val Ser Ala Leu Glu Thr Lys Leu Gly Glu Leu Lys Arg Glu
    50                  55                  60

Leu Ala Asp Leu Ile Ala Ala Gln Lys Leu Ala Ser Lys Pro Val Asp
65                  70                  75                  80

Pro Thr Gly Ile Glu Pro Asp Asp His Leu Lys Glu Lys Ser Ser Leu
                85                  90                  95

Arg Tyr Gly Asn Val Leu Val Val Asn Ser Ile Asp Leu
            100                 105

<210> SEQ ID NO 23
<211> LENGTH: 3351
<212> TYPE: DNA
<213> ORGANISM: Four Corners hantavirus

<400> SEQUENCE: 23
tagtagtaga ctccgcaaga agaagcaaac actgaataaa ggagatacag aatggtaggg      60
tgggtttgca tcttcctcgt ggtccttact actgcaactg ctgggctaac acggaatctt     120
tatgagttga agatagaatg tccacatact gtaggtttag gtcagggtta cgtgacaggt     180
tcagtggaaa ctacacctat tctcttaacg caggtagctg atcttaagat tgagagttct     240
tgtaatttcg atctgcatgt cccggctact actacccaaa aatacaatca ggttgactgg     300
accaaaaaaa gttcaactac agaaagcaca aatgcaggtg caactacatt tgaggctaaa     360
acaaaagaga taaatttaaa aggcacatgt aatattcctc aactacatt tgaagctgca     420
tataaatcaa ggaagacagt aatttgttat gatttagcct gtaatcaaac acattgtctt     480
cctacagtcc atttgattgc tcctgttcaa acgtgcatgt ctgtgcggag ctgtatgata     540
ggtttgctgt caagcaggat tcaagtcata tatgagaaga catactgtgt tacaggtcaa     600
ttaatagagg ggctatgttt catcccaaca catacaattg cactcacaca acctggtcat     660
acctatgata ctatgacatt gccagtgact tgttttttag tagctaaaaa gttgggaaca     720
```

-continued

```
caacttaagc tggctgttga gttagagaaa ctgattactg gtgtgagttg cacagaaaac    780
agctttcaag gttactacat ctgctttatc ggaaaacatt cagagcccct atttgtgcca    840
acaatggaag attataggtc agctgagtta tttacccgta tggttttaaa tccgagaggt    900
gaagatcatg accctgatca aaatggacaa ggcttaatga aatagccgg acctgttaca    960 gctaaggtgc catctacaga aacaacggaa acaatgcaag gaattgcatt tgctggggca   1020
ccgatgtata gctctttctc aactctcgtg aggaaggctg atcctgagta tgtcttctcc   1080
ccaggtataa ttgcagaatc aaatcatagt gtctgtgata agaaaacagt accccttaca   1140
tggacagggt ttttggcagt ttctggagag atagagaaaa taacaggctg tacagtcttc   1200
tgtacattgg caggacctgg tgctagttgt gaagcatact cagaaacagg aatctttaat   1260
ataagctctc ctacttgttt ggtgaataaa gttcaaaaat cagaggctc agaacagaga    1320 atcaacttca tgtgccaaag agttgatcaa gatgttgtag tctattgtaa tgggcaaaag   1380
aaagtcattc ttaccaaaac tctggtcata ggccaatgta tttatacatt cactagttta   1440
ttctcactaa tcctaggagt tgcccattct cttgccgtag agctatgtgt tccaggtctt   1500
catggctggg ctacaacagc attactgatt acttttttgct ttggctggct ccttataccg   1560
acagtcacct taattatact aaagatcctg aggttgctca ctttctcatg ctcacattat   1620
tctacagaat caaaattcaa agttatctta gaaagagtta aggttgaata ccaaaaaaca   1680
atgggctcta tggtgtgtga tatttgccac catgaatgcg aaacagcaaa agaacttgaa   1740
acacataaga aaagctgtcc agaaggtcaa tgcccgtatt gtatgacaat aactgaatcc   1800
actgagatgg ctcttcaagc ccatttttgca atctgtaagt taacaaacag gtttcaggaa   1860
aacttaaaaa aatcattaaa acgcccagaa gtacggaaag gttgttacag gacactggga   1920
gtttttagat acaagagcag atgttatgtt ggtttagtat ggggaattct tttaacaact   1980
gaactgatca tatgggcagc cagtgcagaa acccccttaa tggagtctgg ttggtctgac   2040
acagcgcatg gtgtgggcat aattcctatg aagacagatt tggagcttga ctttgcatcg   2100
gcctcatcat cttcttacag ttataggcga agcttataa accctgctaa tcaagaagaa   2160
acactccctt ttcatttcca gttagacaaa caagtagtgc atgcagagat ccagaaccta   2220
ggacattgga tggatggtac attcaacata aaaactgctt tcactgttta tggggagtgt   2280
aaaaaatatg cctatccttg gcaaacagcc aagtgcttct ttgaaaagga ttatcagtat   2340
gaaacaagtg ggggctgtaa tccaccagac tgtccagggg taggtacagg ttgtacagct   2400
tgtggggtgt atctcgataa gtcccgttcg gttgggaaag catacaagat agtatcactc   2460
aaatacacac ggaaggtgtg tattcaatta aggaacagaa aaacttgtaa acatatagat   2520
gtaaatgatt gcttggttac cccttctgtc aaagtttgta tgatcggtac tatatcaaag   2580
ctccaaccag gtgatacttt gttgttctta ggcccttag agcagggtgg gattatcctt   2640
aagcaatggt gtacaacatc atgtgtgttt ggagaccccg tgatattat gtcaacgaca   2700 agtgggatga ggtgcccaga acatactgga tctttttagaa agatatgtgg gtttgctaca   2760
acaccaacat gtgagtatca aggcaacaca gtgtctgggt tcaaacgcat gatggcaact   2820
cgagattctt tccaatcatt caatgtgaca gaaccacata tcactagcaa ccgacttgag   2880
tggattgatc agatagcag tatcaaagat catattaata tggttttaaa tcgggatgtt   2940
tcctttcagg atctaagtga taacccatgc aaggttgatc tgcatataca atcaattgat   3000
ggggcctggg gttcagggat aggttttacg ttggtatgca ctgtggggct tacagagtgt   3060
gcaaatttta taacttcaat taaagcatgt gattctgcca tgtgttatgg agccacagtg   3120
```

```
acaaatctgc ttagagggtc aaacacagtt agagttgttg gtaaaggtgg gcattctgga      3180
tctttgttta aatgctgcaa tgatactgac tgtaccgaag aaggtttagc agcatctcca      3240
ccacatttag atagggttac aggtcacaat caaatagatt ctgataaagt ttatgatgac      3300
gttgcaccgc cctgtacaat caagtgttgg tttaaaaaat ctggggaatg g               3351
```

<210> SEQ ID NO 24
<211> LENGTH: 23
<212> TYPE: DNA
<213> ORGANISM: Prospect Hill virus

<400> SEQUENCE: 24

```
tagtagtaga ctccgcaaga aga                                               23
```

<210> SEQ ID NO 25
<211> LENGTH: 23
<212> TYPE: DNA
<213> ORGANISM: Puumala virus

<400> SEQUENCE: 25

```
tagtagtaga ctccgcaaga aga                                               23
```

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence:PCR Primer

<400> SEQUENCE: 26

```
tagtagtaga ctccgcaaga aga                                               23
```

<210> SEQ ID NO 27
<211> LENGTH: 23
<212> TYPE: DNA
<213> ORGANISM: Prospect Hill virus

<400> SEQUENCE: 27

```
agattgaatg tcctcatact gta                                               23
```

<210> SEQ ID NO 28
<211> LENGTH: 23
<212> TYPE: DNA
<213> ORGANISM: Puumala virus

<400> SEQUENCE: 28

```
aaatggaatg tccacatact att                                               23
```

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence:PCR Primer

<400> SEQUENCE: 29

```
accatggaat gtcctcatac tgta                                              24
```

<210> SEQ ID NO 30
<211> LENGTH: 24
<212> TYPE: DNA
<213> ORGANISM: Prospect Hill virus -continued

<400> SEQUENCE: 30
tgtgtactgt aatggcatga agaa                                  24

<210> SEQ ID NO 31
<211> LENGTH: 24
<212> TYPE: DNA
<213> ORGANISM: Puumala virus

<400> SEQUENCE: 31
tgtttactgt aatgggatga agaa                                  24

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence:PCR Primer

<400> SEQUENCE: 32
tgtgttactg taatggcgat gaagaa                                26

<210> SEQ ID NO 33
<211> LENGTH: 26
<212> TYPE: DNA
<213> ORGANISM: Prospect Hill virus

<400> SEQUENCE: 33
aagaaggtaa ttcttactaa aaccct                                26

<210> SEQ ID NO 34
<211> LENGTH: 26
<212> TYPE: DNA
<213> ORGANISM: Puumala virus

<400> SEQUENCE: 34
aagaaagtca ttctcaccaa gaccct                                26

<210> SEQ ID NO 35
<211> LENGTH: 28
<212> TYPE: DNA
<213> ORGANISM: Artificial Sequence
<220> FEATURE:
<223> OTHER INFORMATION: Description of Artificial Sequence:PCR Primer

<400> SEQUENCE: 35
aagaagagta cattcttact aaaaccct                              28

<210> SEQ ID NO 36
<211> LENGTH: 18
<212> TYPE: DNA
<213> ORGANISM: Prospect Hill virus

<400> SEQUENCE: 36
acattctgtt ttggctgg                                         18

<210> SEQ ID NO 37
<211> LENGTH: 18
<212> TYPE: DNA
<213> ORGANISM: Puumala virus

<400> SEQUENCE: 37
acattctgtt ttggctgg                                         18

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence:PCR Primer

<400> SEQUENCE: 38
acattctgtt ttggctgg                                              18

<210> SEQ ID NO 39
<211> LENGTH: 21
<212> TYPE: DNA
<213> ORGANISM: Prospect Hill virus

<400> SEQUENCE: 39
atggtctgtg aggtttgtca g                                          21

<210> SEQ ID NO 40
<211> LENGTH: 21
<212> TYPE: DNA
<213> ORGANISM: Puumala virus

<400> SEQUENCE: 40
atggtttgtg aagtgtgtca g                                          21

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence:PCR Primer

<400> SEQUENCE: 41
atggtcttgt gagagtttgt cag                                        23

<210> SEQ ID NO 42
<211> LENGTH: 23
<212> TYPE: DNA
<213> ORGANISM: Prospect Hill virus

<400> SEQUENCE: 42
tttagaaaga aatgtgcatt tgc                                        23

<210> SEQ ID NO 43
<211> LENGTH: 23
<212> TYPE: DNA
<213> ORGANISM: Puumala virus

<400> SEQUENCE: 43
tttagaaaga aatgtgcatt tgc                                        23

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence:PCR Primer

<400> SEQUENCE: 44
tttagaaaga aatgtgcatt tgc                                        23

<210> SEQ ID NO 45
<211> LENGTH: 18
<212> TYPE: DNA

```
<213> ORGANISM: Prospect Hill virus

<400> SEQUENCE: 45
tggtgcatgg ggctcagg                                               18

<210> SEQ ID NO 46
<211> LENGTH: 18
<212> TYPE: DNA
<213> ORGANISM: Puumala virus

<400> SEQUENCE: 46
tggagcatgg ggttcagg                                               18

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence:PCR Primer

<400> SEQUENCE: 47
ttgtagcatg gggcttcagg                                             20

<210> SEQ ID NO 48
<211> LENGTH: 24
<212> TYPE: DNA
<213> ORGANISM: Prospect Hill virus

<400> SEQUENCE: 48
tggtttaaaa agtctgggga atgg                                        24

<210> SEQ ID NO 49
<211> LENGTH: 24
<212> TYPE: DNA
<213> ORGANISM: Puumala virus

<400> SEQUENCE: 49
tggtttaaaa aatcaggtga atgg                                        24

<210> SEQ ID NO 50
<211> LENGTH: 26
<212> TYPE: DNA
<213> ORGANISM: Artificial Sequence
<220> FEATURE:
<223> OTHER INFORMATION: Description of Artificial Sequence:PCR Primer

<400> SEQUENCE: 50
tggtttaaaa aagtctaggg gaatgg                                      26

<210> SEQ ID NO 51
<211> LENGTH: 20
<212> TYPE: DNA
<213> ORGANISM: Prospect Hill virus

<400> SEQUENCE: 51
aattggatgg tagtggcagt                                             20

<210> SEQ ID NO 52
<211> LENGTH: 20
<212> TYPE: DNA
<213> ORGANISM: Puumala virus

<400> SEQUENCE: 52
aattggatgg ttgttgctgt                                             20
```

```
<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence:PCR Primer

<400> SEQUENCE: 53
aattggatgg tatgtgtgca gt                                              22

<210> SEQ ID NO 54
<211> LENGTH: 25
<212> TYPE: DNA
<213> ORGANISM: Prospect Hill virus

<400> SEQUENCE: 54
tagtagactt cgtaaagagc tacta                                           25

<210> SEQ ID NO 55
<211> LENGTH: 25
<212> TYPE: DNA
<213> ORGANISM: Puumala virus

<400> SEQUENCE: 55
tagtagactc cttgaaaagc tacta                                           25

<210> SEQ ID NO 56
<211> LENGTH: 27
<212> TYPE: DNA
<213> ORGANISM: Artificial Sequence
<220> FEATURE:
<223> OTHER INFORMATION: Description of Artificial Sequence:PCR Primer

<400> SEQUENCE: 56
tagtagactt cttagaagaa gctacta                                         27

<210> SEQ ID NO 57
<211> LENGTH: 24
<212> TYPE: DNA
<213> ORGANISM: Prospect Hill virus

<400> SEQUENCE: 57
ggtggaccca gatgacgtta acaa                                            24

<210> SEQ ID NO 58
<211> LENGTH: 24
<212> TYPE: DNA
<213> ORGANISM: Puumala virus

<400> SEQUENCE: 58
agtggacccg gatgacgtta acaa                                            24

<210> SEQ ID NO 59
<211> LENGTH: 25
<212> TYPE: DNA
<213> ORGANISM: Artificial Sequence
<220> FEATURE:
<223> OTHER INFORMATION: Description of Artificial Sequence:PCR Primer

<400> SEQUENCE: 59
ggtggaccca ggatgacgtt aacaa                                           25

<210> SEQ ID NO 60
```

```
<211> LENGTH: 24
<212> TYPE: DNA
<213> ORGANISM: Prospect Hill virus

<400> SEQUENCE: 60
ggtgatgata tgg

```
<220> FEATURE:
<223> OTHER INFORMATION: Description of Artificial Sequence:PCR Primer

<400> SEQUENCE: 67
caacttcatg tgccaaagag t                                               21

<210> SEQ ID NO 68
<211> LENGTH: 25
<212> TYPE: DNA
<213> ORGANISM: Artificial Sequence
<220> FEATURE:
<223> OTHER INFORMATION: Description of Artificial Sequence:PCR Primer

<400> SEQUENCE: 68
ggtggaccca ggatgacgtt aacaa                                           25

<210> SEQ ID NO 69
<211> LENGTH: 25
<212> TYPE: DNA
<213> ORGANISM: Artificial Sequence
<220> FEATURE:
<223> OTHER INFORMATION: Description of Artificial Sequence:PCR Primer

<400> SEQUENCE: 69
tagctcggga tccatagtca tcacc                                           25

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence:PCR Primer

<400> SEQUENCE: 70
caacttcatg tgccaaagag t                                               21

<210> SEQ ID NO 71
<211> LENGTH: 26
<212> TYPE: DNA
<213> ORGANISM: Artificial Sequence
<220> FEATURE:
<223> OTHER INFORMATION: Description of Artificial Sequence:PCR Primer

<400> SEQUENCE: 71
ccattcccca tgactttttt aaacca                                          26

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence:PCR Primer

<400> SEQUENCE: 72
acattctgtt ttggctgg                                                   18

<210> SEQ ID NO 73
<211> LENGTH: 22
<212> TYPE: DNA
<213> ORGANISM: Artificial Sequence
<220> FEATURE:
<223> OTHER INFORMATION: Description of Artificial Sequence:PCR Primer

<400> SEQUENCE: 73
gcaaatgcac atttctttct aa                                              22
```

<210> SEQ ID NO 74
<211> LENGTH: 24
<212> TYPE: DNA
<213> ORGANISM: Artificial Sequence
<220> FEATURE:
<223> OTHER INFORMATION: Description of Artificial Sequence:PCR Primer

<400> SEQUENCE: 74
accatggaat gtcctcatac tgta                                           24

<210> SEQ ID NO 75
<211> LENGTH: 28
<212> TYPE: DNA
<213> ORGANISM: Artificial Sequence
<220> FEATURE:
<223> OTHER INFORMATION: Description of Artificial Sequence:PCR Primer

<400> SEQUENCE: 75
agggttttag taagaattga cctttctt                                       28

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence:PCR Primer

<400> SEQUENCE: 76
tggtagcatg gggcttcagg                                                20

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence:PCR Primer

<400> SEQUENCE: 77
actgccaact aaccatccaa tt                                             22

<210> SEQ ID NO 78
<211> LENGTH: 32
<212> TYPE: DNA
<213> ORGANISM: Artificial Sequence
<220> FEATURE:
<223> OTHER INFORMATION: Description of Artificial Sequence:PCR Primer

<400> SEQUENCE: 78
tacgactaag cttatgacga ccctcaaaga ag                                  32

<210> SEQ ID NO 79
<211> LENGTH: 33
<212> TYPE: DNA
<213> ORGANISM: Artificial Sequence
<220> FEATURE:
<223> OTHER INFORMATION: Description of Artificial Sequence:PCR Primer

<400> SEQUENCE: 79
tggttcctcg aggtcaatgg aatttacatc aag                                 33

<210> SEQ ID NO 80
<211> LENGTH: 31
<212> TYPE: DNA
<213> ORGANISM: Artificial Sequence
<220> FEATURE:
<223> OTHER INFORMATION: Description of Artificial Sequence:PCR Primer

```
<400> SEQUENCE: 80
attgacctcg aggaaccaag tgggcaaaca g                                    31

<210> SEQ ID NO 81
<211> LENGTH: 28
<212> TYPE: DNA
<213> ORGANISM: Artificial Sequence
<220> FEATURE:
<223> OTHER INFORMATION: Description of Artificial Sequence:PCR Primer

<400> SEQUENCE: 81
ggcttctaga gggatccatg tcatcacc                                        28

<210> SEQ ID NO 82
<211> LENGTH: 33
<212> TYPE: DNA
<213> ORGANISM: Artificial Sequence
<220> FEATURE:
<223> OTHER INFORMATION: Description of Artificial Sequence:PCR Primer

<400> SEQUENCE: 82
tactacagtc gacgggatga gccaactcag gga                                  33

<210> SEQ ID NO 83
<211> LENGTH: 33
<212> TYPE: DNA
<213> ORGANISM: Artificial Sequence
<220> FEATURE:
<223> OTHER INFORMATION: Description of Artificial Sequence:PCR Primer

<400> SEQUENCE: 83
tggttcctcg aggtcaatgg aatttacatc aag                                  33

<210> SEQ ID NO 84
<211> LENGTH: 31
<212> TYPE: PRT
<213> ORGANISM: Prospect Hill virus

<400> SEQUENCE: 84

Leu Lys Leu Glu Ser Ser Cys Asn Phe Asp Val His Thr Ser Ser Ala
 1               5                  10                  15

Thr Gln Gln Ala Val Thr Lys Trp Thr Trp Glu Lys Lys Ala Asp
            20                  25                  30

<210> SEQ ID NO 85
<211> LENGTH: 31
<212> TYPE: PRT
<213> ORGANISM: Puumala virus

<400> SEQUENCE: 85

Leu Lys Leu Glu Ser Ser Cys Asn Phe Asp Leu His Thr Ser Thr Ala
 1               5                  10                  15

Gly Gln Gln Ser Phe Thr Lys Trp Thr Trp Glu Ile Lys Gly Asp
            20                  25                  30

<210> SEQ ID NO 86
<211> LENGTH: 433
<212> TYPE: PRT
<213> ORGANISM: Prospect Hill virus

<400> SEQUENCE: 86

Met Ser Gln Leu Arg Glu Thr Gln Glu Glu Ile Thr Arg His Glu Gln
 1               5                  10                  15
```

-continued

```
Gln Leu Val Ile Ala Arg Gln Lys Leu Lys Glu Ala Glu Arg Thr Val
             20                  25                  30
Glu Val Asp Pro Asp Val Asn Lys Ser Thr Leu Gln Ser Arg Arg
         35                  40                  45
Ser Ala Val Ser Thr Leu Glu Asp Lys Leu Ala Glu Phe Lys Arg Gln
 50                  55                  60
Leu Ala Asp Val Ile Ser Arg Gln Lys Met Asp Glu Lys Pro Val Asp
 65                  70                  75                  80
Pro Thr Gly Ile Glu Leu Asp Asp His Leu Lys Glu Arg Ser Ser Leu
                 85                  90                  95
Gln Tyr Gly Asn Val Leu Asp Val Asn Ser Ile Asp Ile Glu Glu Pro
             100                 105                 110
Ser Gly Gln Thr Ala Asp Trp Leu Lys Ile Gly Ser Tyr Ile Ile Glu
         115                 120                 125
Phe Ala Leu Pro Ile Ile Leu Lys Ala Leu His Met Leu Ser Thr Arg
130                 135                 140
Gly Arg Gln Thr Val Lys Glu Asn Lys Gly Thr Arg Ile Arg Phe Lys
145                 150                 155                 160
Asp Asp Ser Ser Tyr Glu Asp Val Asn Gly Ile Arg Arg Pro Lys His
                 165                 170                 175
Leu Tyr Val Ser Met Pro Thr Ala Gln Ser Thr Met Lys Ala Glu Glu
             180                 185                 190
Leu Thr Pro Gly Arg Phe Arg Thr Ile Val Cys Gly Leu Phe Pro Ala
         195                 200                 205
Gln Ile Met Ala Arg Asn Ile Ile Ser Pro Val Met Gly Val Ile Gly
     210                 215                 220
Phe Ala Phe Phe Val Lys Asp Trp Ala Asp Lys Val Lys Ala Phe Leu
225                 230                 235                 240
Asp Gln Lys Cys Pro Phe Leu Lys Ala Glu Pro Arg Pro Gly Gln Pro
                 245                 250                 255
Ala Gly Glu Ala Glu Phe Leu Ser Ser Ile Arg Ala Tyr Leu Met Asn
             260                 265                 270
Arg Gln Ala Val Leu Asp Glu Thr His Leu Pro Asp Ile Asp Ala Leu
         275                 280                 285
Val Glu Leu Ala Ala Ser Gly Asp Pro Thr Leu Pro Asp Ser Leu Glu
     290                 295                 300
Asn Pro His Ala Ala Trp Val Phe Ala Cys Ala Pro Asp Arg Cys Pro
305                 310                 315                 320
Pro Thr Cys Ile Tyr Ile Ala Gly Met Ala Glu Leu Gly Ala Phe Phe
                 325                 330                 335
Ala Ile Leu Gln Asp Met Arg Asn Thr Ile Met Ala Ser Lys Thr Val
             340                 345                 350
Gly Thr Ala Glu Glu Lys Leu Lys Lys Ser Ala Phe Tyr Gln Ser
         355                 360                 365
Tyr Leu Arg Arg Thr Gln Ser Met Gly Ile Gln Leu Asp Gln Arg Ile
     370                 375                 380
Ile Leu Met Tyr Met Ile Glu Trp Gly Asn Glu Val Val Asn His Phe
385                 390                 395                 400
His Leu Gly Asp Asp Met Asp Pro Glu Leu Arg Gln Leu Ala Gln Ala
                 405                 410                 415
Leu Ile Asp Gln Lys Val Lys Glu Ile Ser Asn Gln Glu Pro Leu Lys
             420                 425                 430
```

Ile

<210> SEQ ID NO 87
<211> LENGTH: 433
<212> TYPE: PRT
<213> ORGANISM: Puumala virus

<400> SEQUENCE: 87

```
Met Ser Asp Leu Thr Asp Ile Gln Glu Asp Ile Thr Arg His Glu Gln
 1               5                  10                  15

Gln Leu Ile Val Ala Arg Gln Lys Leu Lys Asp Ala Glu Arg Ala Val
            20                  25                  30

Glu Val Asp Pro Asp Asp Val Asn Lys Asn Thr Leu Gln Ala Arg Gln
        35                  40                  45

Gln Thr Val Ser Ala Leu Glu Asp Lys Leu Ala Asp Tyr Lys Arg Arg
    50                  55                  60

Met Ala Asp Ala Val Ser Arg Lys Lys Met Asp Thr Lys Pro Thr Asp
65                  70                  75                  80

Pro Thr Gly Ile Glu Pro Asp Asp His Leu Lys Glu Arg Ser Ser Leu
                85                  90                  95

Arg Tyr Gly Asn Val Leu Asp Val Asn Ala Ile Asp Ile Glu Glu Pro
            100                 105                 110

Ser Gly Gln Thr Ala Asp Trp Tyr Thr Ile Gly Val Tyr Val Ile Gly
        115                 120                 125

Phe Thr Leu Pro Ile Ile Leu Lys Ala Leu Tyr Met Leu Ser Thr Arg
    130                 135                 140

Gly Arg Gln Thr Val Lys Glu Asn Lys Gly Thr Arg Ile Arg Phe Lys
145                 150                 155                 160

Asp Asp Thr Ser Phe Glu Asp Ile Asn Gly Ile Arg Arg Pro Lys His
                165                 170                 175

Leu Tyr Val Ser Met Pro Thr Ala Gln Ser Thr Met Lys Ala Glu Glu
            180                 185                 190

Leu Thr Pro Gly Arg Phe Arg Thr Ile Val Cys Gly Leu Phe Pro Thr
        195                 200                 205

Gln Ile Gln Val Arg Asn Ile Met Ser Pro Val Met Gly Val Ile Gly
    210                 215                 220

Phe Ser Phe Phe Val Lys Asp Trp Ser Glu Arg Ile Arg Glu Phe Met
225                 230                 235                 240

Glu Lys Glu Cys Pro Phe Ile Lys Pro Glu Val Lys Pro Gly Thr Pro
                245                 250                 255

Ala Gln Glu Ile Glu Met Leu Lys Arg Asn Lys Ile Tyr Phe Met Gln
            260                 265                 270

Arg Gln Asp Val Leu Asp Lys Asn His Val Ala Asp Ile Asp Lys Leu
        275                 280                 285

Ile Asp Tyr Ala Ala Ser Gly Asp Pro Thr Ser Pro Asp Asn Ile Asp
    290                 295                 300

Ser Pro Asn Ala Pro Trp Val Phe Ala Cys Ala Pro Asp Arg Cys Pro
305                 310                 315                 320

Pro Thr Cys Ile Tyr Val Ala Gly Met Ala Glu Leu Gly Ala Phe Phe
                325                 330                 335

Ser Ile Leu Gln Asp Met Arg Asn Thr Ile Met Ala Ser Lys Thr Val
            340                 345                 350

Gly Thr Ala Glu Glu Lys Leu Lys Lys Lys Ser Ser Phe Tyr Gln Ser
        355                 360                 365
```

```
Tyr Leu Arg Arg Thr Gln Ser Met Gly Ile Gln Leu Asp Gln Arg Ile
    370                 375                 380

Ile Leu Leu Phe Met Leu Glu Trp Gly Lys Glu Met Val Asp His Phe
385                 390                 395                 400

His Leu Gly Asp Asp Met Asp Pro Glu Leu Arg Gly Leu Ala Gln Ala
                    405                 410                 415

Leu Ile Asp Gln Lys Val Lys Glu Ile Ser Asn Gln Glu Pro Leu Lys
            420                 425                 430

Ile

<210> SEQ ID NO 88
<211> LENGTH: 410
<212> TYPE: PRT
<213> ORGANISM: Four Corners hantavirus

<400> SEQUENCE: 88

Gly Val Gly Leu Gly Gln Gly Tyr Val Thr Gly Ser Val Glu Thr Thr
1               5                   10                  15

Pro Ile Leu Leu Thr Gln Val Ala Asp Leu Lys Ile Glu Ser Ser Cys
            20                  25                  30

Asn Phe Asp Leu His Val Pro Ala Thr Thr Thr Gln Lys Tyr Asn Gln
            35                  40                  45

Val Asp Trp Thr Lys Lys Ser Ser Thr Thr Glu Ser Thr Asn Ala Gly
        50                  55                  60

Ala Thr Thr Phe Glu Ala Lys Thr Lys Glu Ile Asn Leu Lys Gly Thr
65                  70                  75                  80

Cys Asn Ile Pro Pro Thr Thr Phe Glu Ala Ala Tyr Lys Ser Arg Lys
                85                  90                  95

Thr Val Ile Cys Tyr Asp Leu Ala Cys Asn Gln Thr His Cys Leu Pro
            100                 105                 110

Thr Val His Leu Ile Ala Pro Val Gln Thr Cys Met Ser Val Arg Ser
            115                 120                 125

Cys Met Ile Gly Leu Leu Ser Ser Arg Ile Gln Val Ile Tyr Glu Lys
        130                 135                 140

Thr Tyr Cys Val Thr Gly Gln Leu Ile Glu Gly Leu Cys Phe Ile Pro
145                 150                 155                 160

Thr His Thr Ile Ala Leu Thr Gln Pro Gly His Thr Tyr Asp Thr Met
                165                 170                 175

Thr Leu Pro Val Thr Cys Phe Leu Val Ala Lys Lys Leu Gly Thr Gln
            180                 185                 190

Leu Lys Leu Ala Val Glu Leu Glu Lys Leu Ile Thr Gly Val Ser Cys
        195                 200                 205

Thr Glu Asn Ser Phe Gln Gly Tyr Tyr Ile Cys Phe Ile Gly Lys His
    210                 215                 220

Ser Glu Pro Leu Phe Val Pro Thr Met Glu Asp Tyr Arg Ser Ala Glu
225                 230                 235                 240

Leu Phe Thr Arg Met Val Leu Asn Pro Arg Gly Glu Asp His Asp Pro
                245                 250                 255

Asp Gln Asn Gly Gln Gly Leu Met Arg Ile Ala Gly Pro Val Thr Ala
            260                 265                 270

Lys Val Pro Ser Thr Glu Thr Thr Glu Thr Met Gln Gly Ile Ala Phe
        275                 280                 285

Ala Gly Ala Pro Met Tyr Ser Ser Phe Ser Thr Leu Val Arg Lys Ala
    290                 295                 300
```

-continued

```
Asp Pro Glu Tyr Val Phe Ser Pro Gly Ile Ile Ala Glu Ser Asn His
305                 310                 315                 320

Ser Val Cys Asp Lys Lys Thr Val Pro Leu Thr Trp Thr Gly Phe Leu
                325                 330                 335

Ala Val Ser Gly Glu Ile Glu Lys Ile Thr Gly Cys Thr Val Phe Cys
            340                 345                 350

Thr Leu Ala Gly Pro Gly Ala Ser Cys Glu Ala Tyr Ser Glu Thr Gly
        355                 360                 365

Ile Phe Asn Ile Ser Ser Pro Thr Cys Leu Val Asn Lys Val Gln Lys
    370                 375                 380

Phe Arg Gly Ser Glu Gln Arg Ile Asn Phe Met Cys Gln Arg Val Asp
385                 390                 395                 400

Gln Asp Val Val Val Tyr Cys Asn Gly Gln
                405                 410

<210> SEQ ID NO 89
<211> LENGTH: 1142
<212> TYPE: PRT
<213> ORGANISM: Prospect Hill virus

<400> SEQUENCE: 89

Met Ser Lys Phe Cys Leu Cys Leu Ser Leu Leu Gly Val Leu Leu Leu
  1               5                  10                  15

Gln Val Cys Asp Thr Arg Ser Leu Leu Glu Leu Lys Ile Glu Cys Pro
             20                  25                  30

His Thr Val Gly Leu Gly Gln Gly Leu Val Ile Gly Thr Val Asp Leu
         35                  40                  45

Asn Pro Val Pro Val Glu Ser Val Ser Thr Leu Lys Leu Glu Ser Ser
     50                  55                  60

Cys Asn Phe Asp Val His Thr Ser Ser Ala Thr Gln Gln Ala Val Thr
 65                  70                  75                  80

Lys Trp Thr Trp Glu Lys Lys Ala Asp Thr Ala Glu Thr Ala Lys Ala
                 85                  90                  95

Ala Ser Thr Thr Phe Gln Ser Lys Ser Thr Glu Leu Asn Leu Arg Gly
            100                 105                 110

Leu Cys Val Ile Pro Thr Leu Val Leu Glu Thr Ala Asn Lys Leu Arg
        115                 120                 125

Lys Thr Val Thr Cys Tyr Asp Leu Ser Cys Asn Gln Thr Ala Cys Ile
    130                 135                 140

Pro Thr Val Tyr Leu Ile Ala Pro Ile His Thr Cys Val Thr Thr Lys
145                 150                 155                 160

Ser Cys Leu Leu Gly Leu Gly Thr Gln Arg Ile Gln Val Thr Tyr Glu
                165                 170                 175

Lys Thr Tyr Cys Val Ser Gly Gln Leu Val Glu Gly Thr Cys Phe Asn
            180                 185                 190

Pro Ile His Thr Met Ala Leu Ser Gln Pro Ser His Thr Tyr Asp Ile
        195                 200                 205

Val Thr Ile Pro Val Arg Cys Phe Phe Ile Ala Lys Lys Thr Asn Asp
    210                 215                 220

Asp Thr Leu Lys Ile Glu Lys Gln Phe Glu Thr Ile Leu Glu Lys Ser
225                 230                 235                 240

Gly Cys Thr Ala Ala Asn Ile Lys Gly Tyr Tyr Val Cys Phe Leu Gly
                245                 250                 255

Ala Thr Ser Glu Pro Ile Phe Val Pro Thr Met Asp Asp Phe Arg Ala
            260                 265                 270
```

```
Ser Gln Ile Leu Ser Asp Met Ala Ile Ser Pro His Gly Glu Asp His
        275                 280                 285

Asp Ser Ala Leu Ser Ser Val Ser Thr Phe Arg Ile Ala Gly Lys Leu
        290                 295                 300

Ser Gly Lys Ala Pro Ser Thr Glu Ser Ser Asp Thr Val Gln Gly Val
305                 310                 315                 320

Ala Phe Ser Gly His Pro Leu Tyr Thr Ser Leu Ser Val Leu Ala Ser
                325                 330                 335

Lys Glu Asp Pro Val Tyr Ile Trp Ser Pro Gly Ile Ile Pro Glu Arg
                340                 345                 350

Asn His Thr Val Cys Asp Lys Lys Thr Leu Pro Leu Thr Trp Thr Gly
                355                 360                 365

Tyr Leu Pro Leu Pro Gly Gly Ile Glu Lys Thr Thr Gln Cys Thr Ile
        370                 375                 380

Phe Cys Thr Leu Ala Gly Pro Gly Ala Asp Cys Glu Ala Tyr Ser Asp
385                 390                 395                 400

Thr Gly Ile Phe Asn Ile Ser Ser Pro Thr Cys Leu Ile Asn Arg Val
                405                 410                 415

Gln Arg Phe Arg Gly Ala Glu Gln Ile Lys Phe Val Cys Gln Arg
                420                 425                 430

Val Asp Leu Asp Ile Val Val Tyr Cys Asn Gly Met Lys Lys Val Ile
        435                 440                 445

Leu Thr Lys Thr Leu Val Ile Gly Gln Cys Ile Tyr Thr Phe Thr Ser
        450                 455                 460

Val Phe Ser Leu Met Pro Gly Ile Ala His Ser Leu Ala Val Glu Leu
465                 470                 475                 480

Cys Val Pro Gly Ile His Gly Trp Ser Thr Ile Ala Leu Leu Ala Thr
                485                 490                 495

Phe Cys Phe Gly Trp Leu Leu Ile Pro Ile Ile Ser Leu Val Ser Ile
                500                 505                 510

Lys Ile Met Leu Leu Phe Ala Tyr Met Cys Ser Lys Tyr Ser Asn Asp
        515                 520                 525

Ser Lys Phe Arg Leu Leu Ile Glu Lys Val Lys Gln Glu Tyr Gln Lys
        530                 535                 540

Thr Met Gly Ser Met Val Cys Glu Val Cys Gln Gln Glu Cys Glu Met
545                 550                 555                 560

Ala Lys Glu Leu Glu Ser His Lys Lys Ser Cys Pro Asn Gly Met Cys
                565                 570                 575

Pro Tyr Cys Met Asn Pro Thr Glu Ser Thr Glu Ser Ala Leu Gln Ala
                580                 585                 590

His Phe Lys Val Cys Lys Leu Thr Thr Arg Phe Gln Glu Asn Leu Arg
                595                 600                 605

Lys Ser Leu Asn Pro Tyr Glu Pro Lys Arg Gly Cys Tyr Arg Thr Leu
        610                 615                 620

Ser Val Phe Arg Tyr Arg Ser Arg Cys Phe Val Gly Leu Val Trp Cys
625                 630                 635                 640

Ile Leu Leu Val Leu Glu Leu Val Ile Trp Ala Ala Ser Ala Asp Thr
                645                 650                 655

Val Glu Ile Lys Thr Gly Trp Thr Asp Thr Ala His Gly Ala Gly Val
                660                 665                 670

Ile Pro Leu Lys Ser Asp Leu Glu Leu Asp Phe Ser Leu Pro Ser Ser
        675                 680                 685
```

```
Ala Thr Tyr Ile Tyr Arg Arg Asp Leu Gln Asn Pro Ala Asn Glu Gln
    690                 695                 700

Glu Arg Ile Pro Phe His Phe Gln Leu Gln Arg Gln Val Ile His Ala
705                 710                 715                 720

Glu Ile Gln Asn Leu Gly His Trp Met Asp Gly Thr Phe Asn Leu Lys
                725                 730                 735

Thr Ser Phe His Cys Tyr Gly Ala Cys Glu Lys Tyr Ala Tyr Pro Trp
            740                 745                 750

Gln Thr Ala Lys Cys Phe Leu Glu Lys Asp Tyr Glu Phe Glu Thr Gly
            755                 760                 765

Trp Gly Cys Asn Pro Gly Asp Cys Pro Gly Val Gly Thr Gly Cys Thr
        770                 775                 780

Ala Cys Gly Val Tyr Leu Asp Lys Leu Arg Ser Val Gly Lys Val Phe
785                 790                 795                 800

Lys Val Ile Ser Leu Lys Phe Thr Arg Arg Val Cys Ile Gln Leu Gly
                805                 810                 815

Ser Glu Gln Ser Cys Lys Thr Ile Asp Ser Asn Asp Cys Leu Met Thr
            820                 825                 830

Thr Ser Val Lys Val Cys Met Ile Gly Thr Val Ser Lys Phe Gln Pro
        835                 840                 845

Gly Asp Thr Leu Leu Phe Leu Gly Pro Leu Glu Glu Gly Gly Ile Ile
    850                 855                 860

Phe Lys Gln Trp Cys Thr Thr Thr Cys His Phe Gly Asp Pro Gly Asp
865                 870                 875                 880

Ile Met Ser Thr Pro Gln Gly Met Gln Cys Pro Glu His Thr Gly Ala
                885                 890                 895

Phe Arg Lys Lys Cys Ala Phe Ala Thr Met Pro Thr Cys Glu Tyr Asp
            900                 905                 910

Gly Asn Thr Leu Ser Gly Tyr Gln Arg Met Leu Ala Thr Arg Asp Ser
        915                 920                 925

Phe Gln Ser Phe Asn Ile Thr Glu Pro His Ile Thr Ser Asn Ser Leu
    930                 935                 940

Glu Trp Val Asp Pro Asp Ser Ser Leu Lys Asp His Ile Asn Leu Val
945                 950                 955                 960

Val Asn Arg Asp Val Ser Phe Gln Asp Leu Ser Glu Asn Pro Cys Gln
                965                 970                 975

Val Gly Val Ala Val Ser Ser Ile Asp Gly Ala Trp Gly Ser Gly Val
            980                 985                 990

Gly Phe Asn Leu Val Cys Ser Val Ser Leu Thr Glu Cys Ala Ser Phe
        995                 1000                1005

Leu Thr Ser Ile Lys Ala Cys Asp Ala Ala Met Cys Tyr Gly Ala Thr
    1010                1015                1020

Thr Ala Asn Leu Val Arg Gly Gln Asn Thr Val His Ile Leu Gly Lys
1025                1030                1035                1040

Gly Gly His Ser Gly Ser Lys Phe Met Cys Cys His Ser Thr Glu Cys
                1045                1050                1055

Ser Ser Thr Gly Leu Thr Ala Ala Ala Pro His Leu Asp Arg Val Thr
            1060                1065                1070

Gly Tyr Asn Val Ile Asp Asn Asp Lys Val Phe Asp Asp Gly Ser Pro
        1075                1080                1085

Glu Cys Gly Val His Cys Trp Phe Lys Lys Ser Gly Glu Trp Leu Met
    1090                1095                1100

Gly Ile Leu Ser Gly Asn Trp Met Val Val Ala Val Leu Val Val Leu
```

-continued

```
1105                1110                1115                1120
Leu Ile Leu Ser Ile Phe Leu Phe Ser Leu Cys Cys Pro Arg Arg Val
                1125                1130                1135
Val His Lys Lys Ser Ser
            1140
```

<210> SEQ ID NO 90
<211> LENGTH: 1148
<212> TYPE: PRT
<213> ORGANISM: Puumala virus

<400> SEQUENCE: 90

```
Met Gly Glu Leu Ser Pro Val Cys Leu Cys Leu Leu Leu Gln Gly Leu
 1               5                  10                  15

Leu Leu Cys Asn Thr Gly Ala Ala Arg Asn Leu Asn Glu Leu Lys Met
            20                  25                  30

Glu Cys Pro His Thr Ile Arg Leu Gly Gln Gly Leu Val Val Gly Ser
        35                  40                  45

Val Glu Leu Pro Ser Leu Pro Ile Gln Gln Val Glu Thr Leu Lys Leu
 50                  55                  60

Glu Ser Ser Cys Asn Phe Asp Leu His Thr Ser Thr Ala Gly Gln Gln
 65                  70                  75                  80

Ser Phe Thr Lys Trp Thr Trp Glu Ile Lys Gly Asp Leu Ala Glu Asn
                85                  90                  95

Thr Gln Ala Ser Ser Thr Ser Phe Gln Thr Lys Ser Ser Glu Val Asn
            100                 105                 110

Leu Arg Gly Leu Cys Leu Ile Pro Thr Leu Val Val Glu Thr Ala Ala
        115                 120                 125

Arg Met Arg Lys Thr Ile Ala Cys Tyr Asp Leu Ser Cys Asn Gln Thr
130                 135                 140

Val Cys Gln Pro Thr Val Tyr Leu Met Gly Pro Ile Gln Thr Cys Ile
145                 150                 155                 160

Thr Thr Lys Ser Cys Leu Leu Ser Leu Gly Asp Gln Arg Ile Gln Val
                165                 170                 175

Asn Tyr Glu Lys Thr Tyr Cys Val Ser Gly Gln Leu Val Glu Gly Ile
            180                 185                 190

Cys Phe Asn Pro Ile His Thr Met Ala Leu Ser Gln Pro Ser His Thr
        195                 200                 205

Tyr Asp Ile Met Thr Met Val Arg Cys Phe Leu Val Ile Lys Lys
    210                 215                 220

Val Thr Ser Gly Asp Ser Met Lys Ile Glu Lys Asn Phe Glu Thr Leu
225                 230                 235                 240

Val Gln Lys Asn Gly Cys Thr Ala Asn Asn Phe Gln Gly Tyr Tyr Ile
                245                 250                 255

Cys Leu Ile Gly Ser Ser Glu Pro Leu Tyr Val Pro Ala Leu Asp
            260                 265                 270

Asp Tyr Arg Ser Ala Glu Val Leu Ser Arg Met Ala Phe Ala Pro His
        275                 280                 285

Gly Glu Asp His Asp Ile Glu Lys Asn Ala Val Ser Ala Met Arg Ile
    290                 295                 300

Ala Gly Lys Val Thr Gly Lys Ala Pro Ser Thr Glu Ser Ser Asp Thr
305                 310                 315                 320

Val Gln Gly Ile Ala Phe Ser Gly Ser Pro Leu Tyr Thr Ser Thr Gly
                325                 330                 335
```

-continued

| | | | | | | | | | | | |
|---|---|---|---|---|---|---|---|---|---|---|---|
|Val|Leu|Thr|Ser|Lys|Asp|Asp|Pro|Val|Tyr|Ile|Trp|Ala|Pro|Gly|Ile|
| | |340| | | |345| | | | |350|

Val Leu Thr Ser Lys Asp Asp Pro Val Tyr Ile Trp Ala Pro Gly Ile
              340             345                 350

Ile Met Glu Gly Asn His Ser Ile Cys Glu Lys Lys Thr Leu Pro Leu
              355             360                 365

Thr Trp Thr Gly Phe Ile Ser Leu Pro Gly Glu Ile Glu Lys Thr Thr
              370             375             380

Gln Cys Thr Val Phe Cys Thr Leu Ala Gly Pro Gly Ala Asp Cys Glu
385               390             395                 400

Ala Tyr Ser Glu Thr Gly Ile Phe Asn Ile Ser Ser Pro Thr Cys Leu
              405             410                 415

Ile Asn Arg Val Gln Arg Phe Arg Gly Ser Glu Gln Gln Ile Lys Phe
              420             425                 430

Val Cys Gln Arg Val Asp Met Asp Ile Thr Val Tyr Cys Asn Gly Met
              435             440                 445

Lys Lys Val Ile Leu Thr Lys Thr Leu Val Ile Gly Gln Cys Ile Tyr
              450             455                 460

Thr Phe Thr Ser Ile Phe Ser Leu Ile Pro Gly Val Ala His Ser Leu
465               470             475                 480

Ala Val Glu Leu Cys Val Pro Gly Leu His Gly Trp Ala Thr Met Leu
              485             490                 495

Leu Leu Leu Thr Phe Cys Phe Gly Trp Val Leu Ile Pro Thr Ile Thr
              500             505                 510

Met Ile Leu Leu Lys Ile Leu Ile Ala Phe Ala Tyr Leu Cys Ser Lys
              515             520                 525

Tyr Asn Thr Asp Ser Lys Phe Arg Ile Leu Ile Glu Lys Val Lys Arg
              530             535             540

Glu Tyr Gln Lys Thr Met Gly Ser Met Val Cys Glu Val Cys Gln Tyr
545               550             555                 560

Glu Cys Glu Thr Ala Lys Glu Leu Glu Ser His Arg Lys Ser Cys Ser
              565             570                 575

Ile Gly Ser Cys Pro Tyr Cys Leu Asn Pro Ser Glu Ala Thr Thr Ser
              580             585                 590

Ala Leu Gln Ala His Phe Lys Val Cys Lys Leu Thr Ser Arg Phe Gln
              595             600                 605

Glu Asn Leu Arg Lys Ser Leu Thr Val Tyr Glu Pro Met Gln Gly Cys
              610             615             620

Tyr Arg Thr Leu Ser Leu Phe Arg Tyr Arg Ser Arg Phe Phe Val Gly
625               630             635                 640

Leu Val Trp Cys Val Leu Leu Val Leu Glu Leu Ile Val Trp Ala Ala
              645             650                 655

Ser Ala Glu Thr Gln Asn Leu Asn Ala Gly Trp Thr Asp Thr Ala His
              660             665                 670

Gly Ser Gly Ile Ile Pro Met Lys Thr Asp Leu Glu Leu Asp Phe Ser
              675             680                 685

Leu Pro Ser Ser Ala Ser Tyr Thr Tyr Arg Arg Gln Leu Gln Asn Pro
              690             695             700

Ala Asn Glu Gln Glu Lys Ile Pro Phe His Leu Gln Leu Ser Lys Gln
705               710             715                 720

Val Ile His Ala Glu Ile Gln His Leu Gly His Trp Met Asp Ala Thr
              725             730                 735

Phe Asn Leu Lys Thr Ala Phe His Cys Tyr Gly Ser Cys Glu Lys Tyr
              740             745                 750

Ala Tyr Pro Trp Gln Thr Ala Gly Cys Phe Ile Glu Lys Asp Tyr Glu

-continued

```
                     755                 760                 765
Tyr Glu Thr Gly Trp Gly Cys Asn Pro Pro Asp Cys Pro Gly Val Gly
        770                 775                 780

Thr Gly Cys Thr Ala Cys Gly Val Tyr Leu Asp Lys Leu Lys Ser Val
785                 790                 795                 800

Gly Lys Val Phe Lys Ile Val Ser Leu Arg Tyr Thr Arg Lys Val Cys
                805                 810                 815

Ile Gln Leu Gly Thr Glu Gln Thr Cys Lys Thr Val Asp Ser Asn Asp
                820                 825                 830

Cys Leu Ile Thr Thr Ser Val Lys Val Cys Leu Ile Gly Thr Ile Ser
                835                 840                 845

Lys Phe Gln Pro Ser Asp Thr Leu Leu Phe Leu Gly Pro Leu Gln Gln
        850                 855                 860

Gly Gly Leu Ile Phe Lys Gln Trp Cys Thr Thr Thr Cys Gln Phe Gly
865                 870                 875                 880

Asp Pro Gly Asp Ile Met Ser Thr Pro Thr Gly Met Lys Cys Pro Glu
                885                 890                 895

Leu Asn Gly Ser Phe Arg Lys Lys Cys Ala Phe Ala Thr Thr Pro Val
                900                 905                 910

Cys Gln Phe Asp Gly Asn Thr Ile Ser Gly Tyr Lys Arg Met Ile Ala
        915                 920                 925

Thr Lys Asp Ser Phe Gln Ser Phe Asn Val Thr Glu Pro His Ile Ser
        930                 935                 940

Thr Ser Ala Leu Glu Trp Ile Asp Pro Asp Ser Ser Leu Arg Asp His
945                 950                 955                 960

Ile Asn Val Ile Val Ser Arg Asp Leu Ser Phe Gln Asp Leu Ser Glu
                965                 970                 975

Thr Pro Cys Gln Ile Asp Leu Ala Thr Ala Ser Ile Asp Gly Ala Trp
                980                 985                 990

Gly Ser Gly Val Gly Phe Asn Leu Val Cys Thr Val Ser Leu Thr Glu
                995                 1000                1005

Cys Ser Ala Phe Leu Thr Ser Ile Lys Ala Cys Asp Ala Ala Met Cys
    1010                1015                1020

Tyr Gly Ser Thr Thr Ala Asn Leu Val Arg Gly Gln Asn Thr Ile His
1025                1030                1035                1040

Ile Val Gly Lys Gly Gly His Ser Gly Ser Lys Phe Met Cys Cys His
                1045                1050                1055

Asp Thr Lys Cys Ser Ser Thr Gly Leu Val Ala Ala Ala Pro His Leu
            1060                1065                1070

Asp Arg Val Thr Gly Tyr Asn Gln Ala Asp Ser Asp Lys Ile Phe Asp
        1075                1080                1085

Asp Gly Ala Pro Glu Cys Gly Met Ser Cys Trp Phe Lys Lys Ser Gly
    1090                1095                1100

Glu Trp Ile Leu Gly Val Leu Asn Gly Asn Trp Met Val Val Ala Val
1105                1110                1115                1120

Leu Val Val Leu Leu Ile Leu Ser Ile Leu Leu Phe Thr Leu Cys Cys
                1125                1130                1135

Pro Arg Arg Pro Ser Tyr Arg Lys Glu His Lys Pro
            1140                1145
```